(12) United States Patent
Martel

(10) Patent No.: US 8,579,795 B2
(45) Date of Patent: Nov. 12, 2013

(54) LIGHT MODULATION DEVICE AND SYSTEM

(76) Inventor: Alain Anadi Martel, St-Adele (CA)

(*) Notice: Subject to any disclaimer, the term of this patent is extended or adjusted under 35 U.S.C. 154(b) by 938 days.

(21) Appl. No.: 12/598,296

(22) PCT Filed: Apr. 28, 2008

(86) PCT No.: PCT/CA2008/000806
§ 371 (c)(1),
(2), (4) Date: Oct. 30, 2009

(87) PCT Pub. No.: WO2008/131553
PCT Pub. Date: Nov. 6, 2008

(65) Prior Publication Data
US 2010/0130812 A1    May 27, 2010

Related U.S. Application Data

(60) Provisional application No. 60/924,066, filed on Apr. 30, 2007.

(51) Int. Cl.
*A61M 21/00* (2006.01)
(52) U.S. Cl.
USPC ............... 600/27; 600/26; 345/690; 362/811; 362/257; 362/269; 362/801; 307/10.8; 347/135
(58) Field of Classification Search
USPC ............. 600/27, 26; 362/811, 257, 269, 801; 307/10.8; 347/135; 345/690
See application file for complete search history.

(56) References Cited

U.S. PATENT DOCUMENTS

| | | | | |
|---|---|---|---|---|
| 4,315,502 A * | 2/1982 | Gorges | | 600/27 |
| 5,070,399 A | 12/1991 | Martel | | |
| 5,403,261 A * | 4/1995 | Shimizu et al. | | 600/27 |
| 6,150,774 A * | 11/2000 | Mueller et al. | | 315/291 |
| 6,720,743 B2 | 4/2004 | Yano et al. | | |
| 2002/0198438 A1 * | 12/2002 | Cromer et al. | | 600/27 |

OTHER PUBLICATIONS

Light Modulation: A New Way of Looking at Light, Martel Professional Lighting Design Magazine No. 57 Sep./Oct. 2007 (Found online at http://www.via-verlag.com/1542.0.html?©L=1 or: http://www.sensora.com/new/images/documents/light_modulation_pld_magazine.pdf).

The Sensora: A Multi-Sensorial Therapeutic Device, Martel Auditory / Visual Stimulation Journal, vol. 1, #3, Sprint '01 (Found online at: http://www.mindmachines.com/FreeJournal/avsj1.3%20free.pdf or: http://www.sensora.com/new/images/documents/sensora_technical_article.pdf).

* cited by examiner

*Primary Examiner* — Christine Matthews
*Assistant Examiner* — Sunita Reddy
(74) *Attorney, Agent, or Firm* — Fish & Richardson P.C.

(57) ABSTRACT

Light modulation devices are provided. At least one Low Frequency Oscillator (LFO) is used to create an oscillating signal used to drive an intensity parameter, a color parameter or both in a light modulator. The oscillating signal may be mixed with a base signal. The modulated signal driving either of the intensity or color parameters may be simple or complex. Systems having a plurality of light projection devices, each associated with a corresponding light modulation device, are also provided. Such Light modulation systems may be used for a variety of applications.

16 Claims, 26 Drawing Sheets

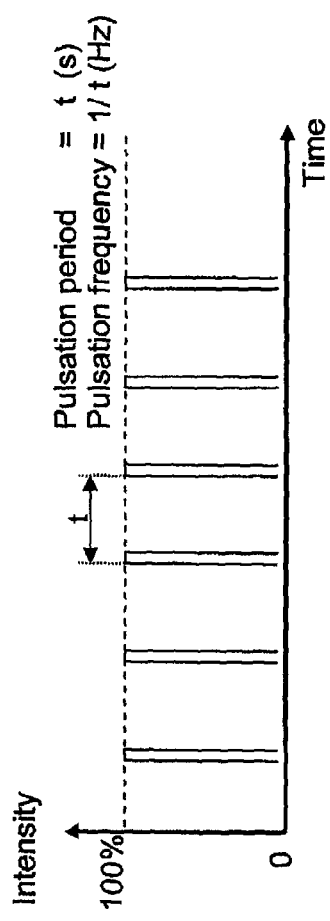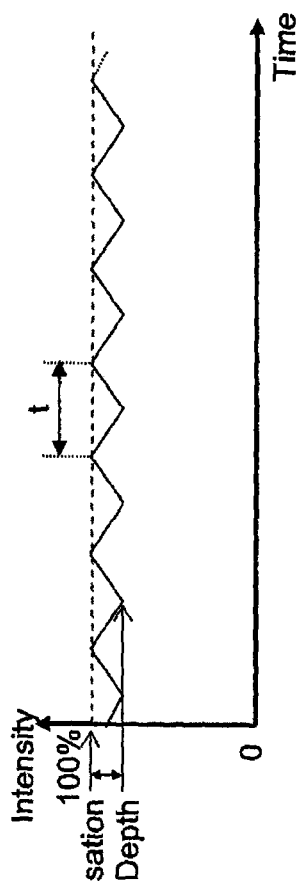
FIG. 1 (Prior Art)
FIG. 2 (Prior Art)

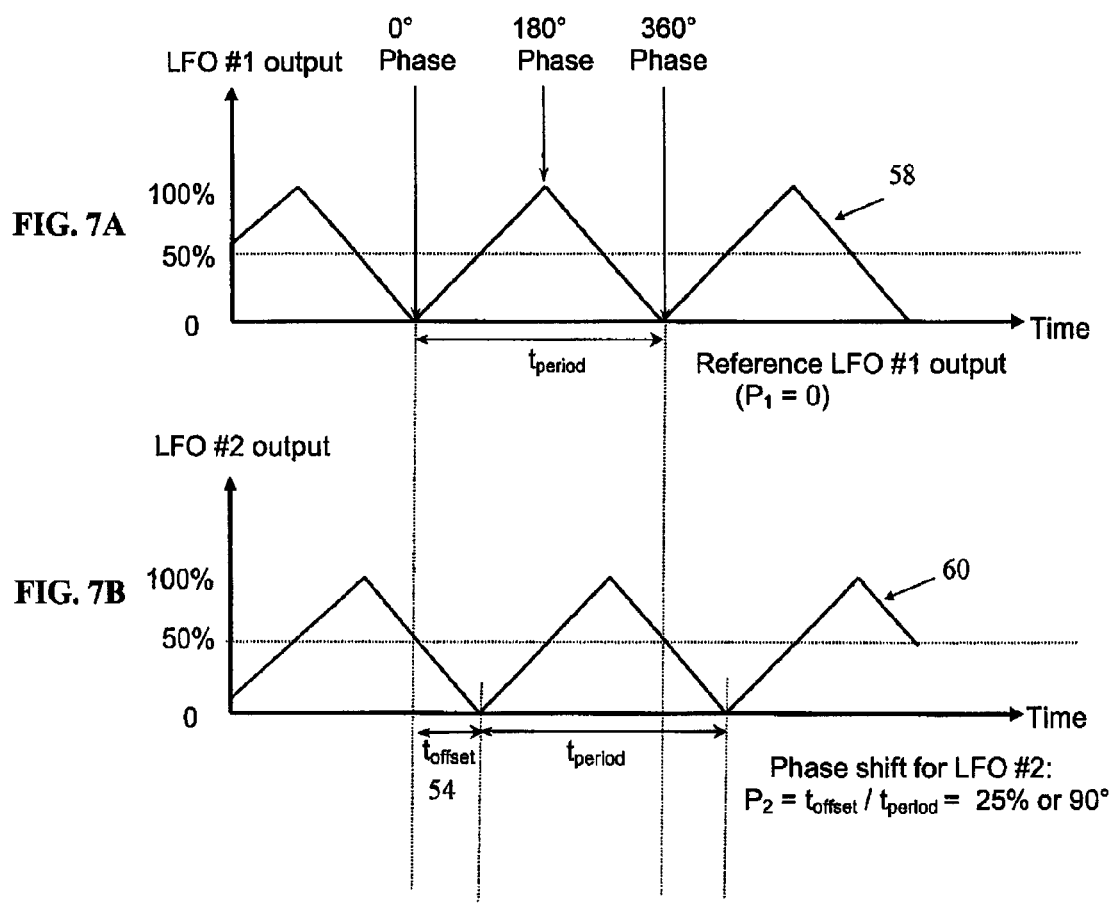

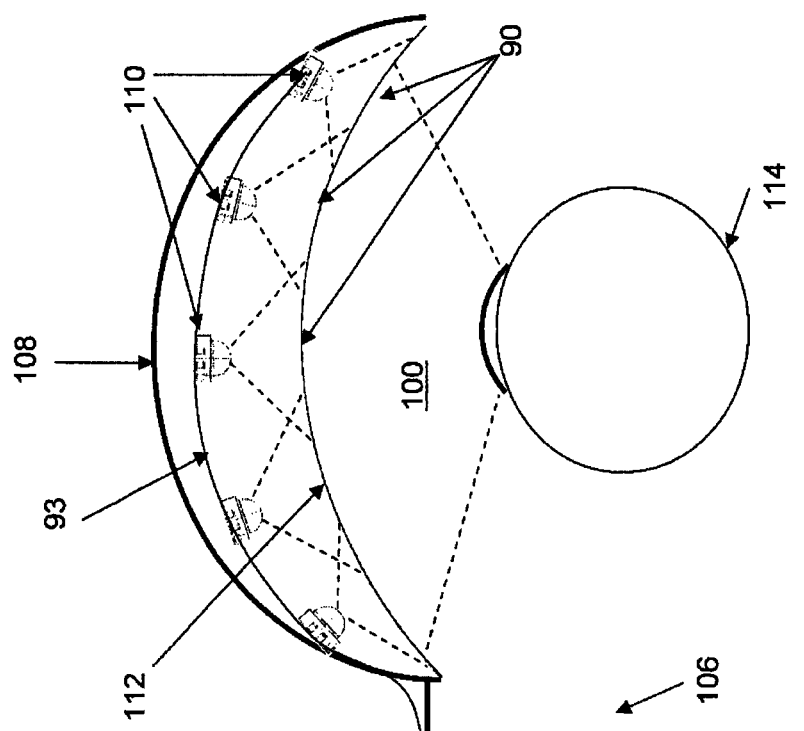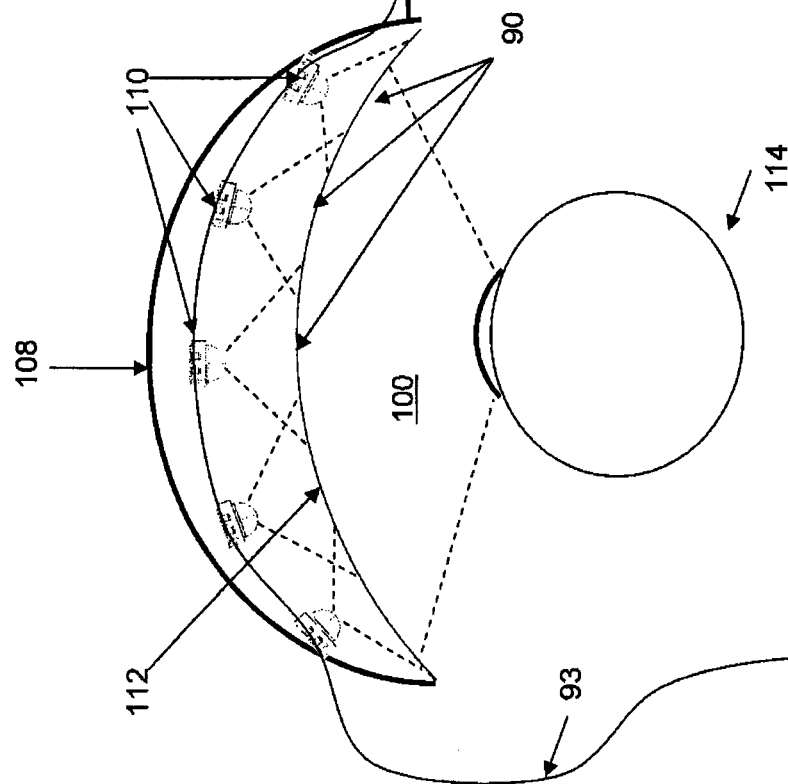
FIG. 28

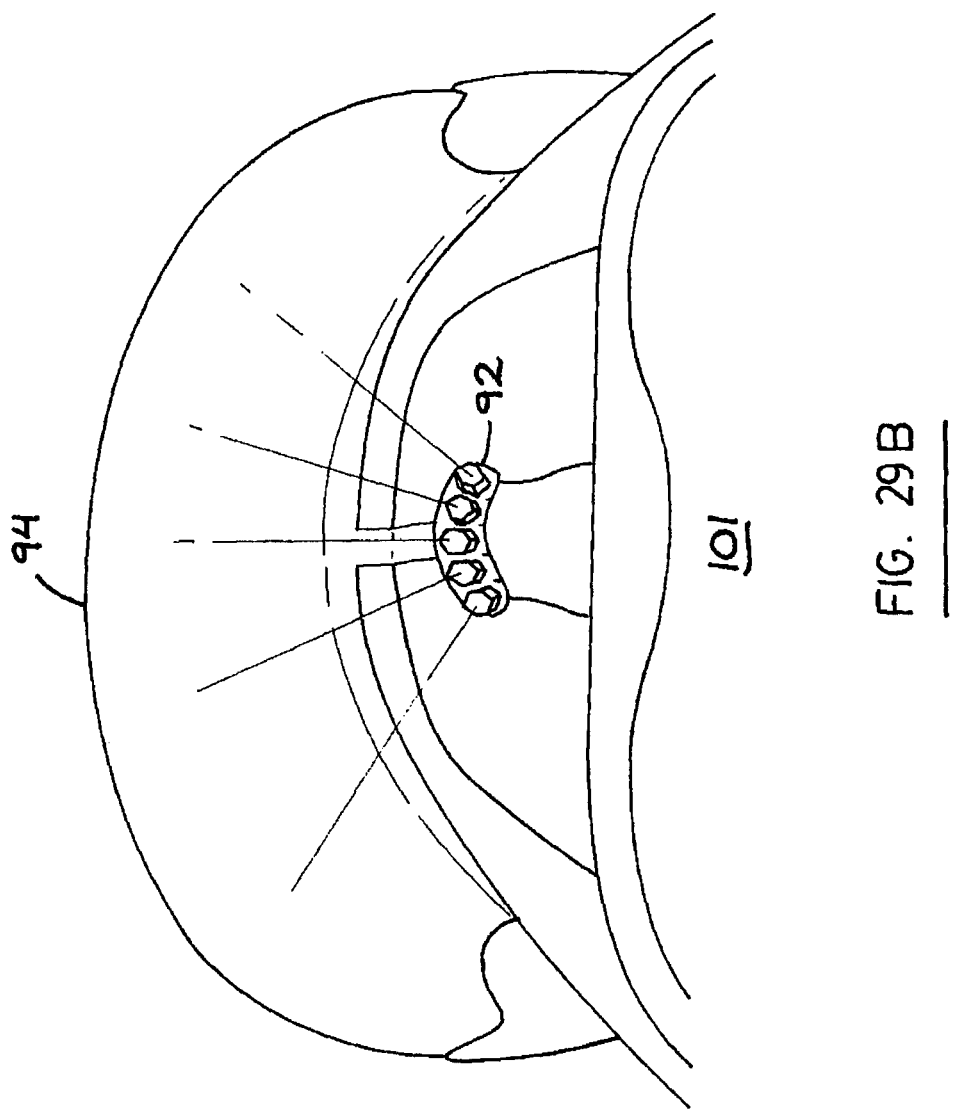

LIGHT MODULATION DEVICE AND SYSTEM

CROSS REFERENCE TO PRIOR APPLICATIONS

This is a U.S. National Phase application under 35 U.S.C. §371 of International Patent Application No. PCT/CA2008/000806, filed Apr. 28, 2008, and claims the benefit of U.S. Provisional Application No. 60/924,066, filed Apr. 30, 2007 both of which are incorporated by reference herein. The International Application published in English on Nov. 6, 2008 as WO 2008/131553 under PCT Article 21(2).

FIELD OF THE INVENTION

The present invention generally relates to light projection, and more particularly concerns systems and devices for modulating projected light.

BACKGROUND OF THE INVENTION

Many visually interesting lighting effects can be obtained by cyclically pulsing light intensity and/or color. For example, many fundamental biological phenomena are related to frequencies in the range of 0.01 Hz and 100 Hz, and their pulsations resonate deeply within human perception. For example, it is well established that when one is exposed to light pulsations within the frequency range of typical brainwaves (approximately 2 Hz to 30 Hz), the brain has a tendency to eventually fall in synchronism with the light pulsations: this phenomenon is known as photic brainwave entrainment. Since different brainwave frequencies are associated to different mind states, it follows that light pulsations can have an influence on mood and state of mind. As another example, pulsations near the typical heartbeat frequency of 1.2 Hz usually strongly attract the attention. As yet another example pulsations at 7.8 Hz, a frequency known as the "Schumann Resonance" which relates to the resonance frequency of the electromagnetic field surrounding the Earth, are perceived as very soothing by most people Light pulsations are already commonly generated in parts of this frequency range with stroboscope-type luminaires such as seen in discotheques or ambiance lighting systems. However, such systems usually generate crude on/off light pulses, as shown in FIG. 1 (PRIOR ART), which can trigger epileptic episodes in some individuals. Current research indicates that 1 in 20,000 adults over 25 years of age have epileptic photosensitivity to pulsing light, without necessarily being aware of it. While this risk associated to standard stroboscopic light pulsations is minimal, it cannot be ignored in lighting applications for the general public.

Extensive psychophysiological research allows us to specify the arousing, relaxing, awareness sharpening, or pacifying effects of various colors. Such research originates in the early work of pioneers such as Dinshah Ghadiali (1863-1966) with his Spectro-Chrome Color Therapy system, and includes treatment modalities such as Syntonic Optometry as developed by Dr. Spitler from 1927. More recent examples include the research of Dr. John Nash Ott (author of "Health and Light", 1973), Dr. Fritz Hollowich (author of "The influence of ocular light perception on metabolism in man and animal", 1969) and Jacob Liberman (Light: Medecine of the Future", 1984). For example, it is well established that so-called cool colors (in the green-blue spectrum) have a tendency to stimulate the parasympathetic portion of the autonomous nervous system (ANS), leading to reduced pulse rate and relaxation. Conversely, so-called warm colors (in the red-orange-yellow spectrum) have a tendency to stimulate the sympathetic portion of the ANS, leading to increased pulse rate and arousal. Intermediate colors (lime and magenta) have a tendency to bring balance and equilibrium between both portions of the ANS. Due to limitations of existing colored light generation technology, most existing color therapy systems have been making use of the application of single static colors, sometimes presented in sequences of chosen colors.

Combining the effect of color with brainwave photic driving has been shown to have great therapeutic potential. Previous inventions making use of this combination include the Photron and Lumitron by John Downing (1984) and the Color Receptivity Trainer by Jacob Liberman (1991). However these devices can only present a single color combined with a single stroboscopically pulsing frequency, with a changing of either parameter requiring a manual intervention.

There may be therapeutic benefits in presenting more complex light projections involving the simultaneous presentation of more than one color, or sequences of colors in a more rapid succession than that allowed by manual control (e.g. more than once per second). Furthermore, there may be therapeutic benefits to combining colors with brainwave pulsations of the colored light intensity without incurring the discomfort of stroboscopic flashes or the risk of epileptic complications. As will be shown below, such modulated light projections can prove particularly effective to induce relaxing, energizing or balancing effects in humans and animals. Through facilitating the induction of a state of deep relaxation, they can also prove particularly effective in reducing stress levels. It is well-known in medical science that stress is a major contributor in a wide variety of health problems: recent research suggests that anywhere from 60 to 90 percent of illness is stress-related. The above-described modulated light projections may therefore assist in the treatment of pathologies generated by excessive stress of the nervous system.

Prior art in the field of light modulation includes U.S. Pat. No. 5,070,399 (MARTEL) entitled "Light Color and Intensity Modulation System", issued in 1991, which describes a system comprising a color scaling device receiving a hue control signal and producing a plurality of color component signals being supplied as the output to color light projectors, and one LFO whose output is an intensity modulation signal for varying the intensity of the plurality of color component signals. While such a system is capable of performing basic light modulation as shown in FIG. 2 (PRIOR ART), its capabilities are limited to a single type of visual effect, i.e., the intensity modulation with one frequency.

There remains however a need for improved systems in this field.

SUMMARY OF THE INVENTION

In accordance with a first aspect of the invention, there is provided a light modulation device for generating modulated color component output signals adapted for use by a light projection device, for modulating light projected thereby.

The light modulation device first includes a light modulator, generating the color component output signals according to an intensity parameter and a color parameter. The color parameter is controlled by a modulated color signal.

The light modulation device further includes a color modulation generator for generating the modulated color signal. The color modulation generator is in communication with the light modulator for providing the modulated color signal thereto. The color modulation generator has a main Low Frequency Oscillator (LFO) generating an oscillating signal and mixing means for mixing this oscillating to signal of the main LFO with a base color signal, thereby providing the modulated color signal.

In accordance with another aspect of the invention, there is also provided a light modulation device for generating modulated color component output signals adapted for use by a light projecting system for modulating light projected thereby, the light modulation device also includes a light modulator generating the color component output signals according to an intensity parameter and a color parameter. At least one of the intensity and color parameters is controlled by a corresponding complex modulated signal. The light modulation device includes a complex modulation generator generating the complex modulated signal, the complex modulation generator being in communication with the light modulator for providing the complex modulated signal thereto. The complex modulation generator has a plurality of Low Frequency Oscillators (LFO) each generating an oscillating signal, the complex modulated signal resulting from a combination of the oscillating signals of each of these LFOs.

In accordance with yet another aspect of the present invention, there is also provided a light modulation system for creating non-representational dynamic patterns of light. The system includes a plurality of colored light projection devices, each being adapted to generate a colored light in a corresponding projection zone. The system further includes a plurality of light modulation devices each being operatively connected to a corresponding projecting device, for providing thereto modulated color component output signals for modulating the corresponding colored light.

Each light modulation device includes a light modulator generating the color component output signals according to an intensity parameter and a color parameter. At least one of the intensity and color parameter is controlled by a corresponding modulated signal. Each light modulation device also includes a modulation generator for generating the corresponding modulated signal, the modulation generator being in communication with the light modulator for providing the modulated signal thereto. The modulation generator has a main Low Frequency Oscillator (LFO) generating an oscillating signal, and mixing means for mixing this oscillating signal of the main LFO with a base signal, thereby providing the modulated signal.

The system also includes a control unit for controlling each of the modulation devices so that the projection zones create together the dynamic patterns of light.

The system above could be used for a variety of applications, such as, non-exhaustively:
  mounted on a well-being chair or bed, the projecting devices being adapted to project the dynamic patterns of light in a field of view of a user.
  in a relaxation room, the projecting devices being are adapted to project the dynamic patterns of light in a field of view of a user.
  for stage lighting.
  for architectural structure lighting.
  integrated inside a wearable light device, such as goggles, adapted to cover the field of view of a user with the dynamic patterns of light.

In accordance with another aspect of the invention, there is also provided a system including a well-being chair for receiving a user thereon, the well-being chair having a head portion for receiving a head of said user, a projection shell mounted over the head portion of the well-being chair, and a light modulation system as defined herein mounted proximate said head portion and positioned to project the non-representational dynamic patterns of light inside said projection shell.

In accordance with yet another aspect of the invention there is also provided a system having a headwear implement for wearing on a head of a user, the headwear implement including a projection shell extending in a field of view of the user. A light modulation system is defined herein is mounted on the headwear implement and positioned to project the non-representational dynamic patterns of light inside the projection shell.

In accordance with another aspect of the invention, there is provided a method for generating non-representational dynamic patterns of light, said method comprising:
a) providing a plurality of colored light projection devices, each being adapted to generate a colored light in a corresponding projection zone;
b) providing modulated color component output signals to each of said light projection devices, comprising:
  i) generating said color component output signals according to an intensity parameter and a color parameter, at least one of said intensity and color parameter being controlled by a corresponding modulated signal; and
  ii) for each of said corresponding modulated signal, generating an oscillating signal using a main Low Frequency Oscillator (LFO), and mixing said oscillating signal of the main LFO with a base signal, thereby providing the modulated signal; and
c) controlling each of said modulation devices so that the projection zones create together said dynamic patterns of light.

In accordance with yet another aspect of the present invention, there is further provided a method for manufacturing a light modulation system for creating non-representational dynamic patterns of light, said method comprising the assembly of electronic components capable of performing the function of:
  providing a plurality of colored light projection devices, each being adapted to generate a colored light in a corresponding projection zone;
  providing a plurality of light modulation devices and operatively connected each said light modulation device to a corresponding projecting device for providing thereto modulated color component output signals for modulating the corresponding colored light, each light modulation device comprising:
    a light modulator generating said color component output signals according to an intensity parameter and a color parameter, at least one of said intensity and color parameter being controlled by a corresponding modulated signal; and
    a modulation generator for generating the corresponding modulated signal, the modulation generator being in communication with the light modulator for providing the modulated signal thereto, said modulation generator having a main Low Frequency Oscillator (LFO) generating an oscillating signal and mixing means for mixing said oscillating signal of the main LFO with a base signal, thereby providing said modulated signal; and
  providing a control unit for controlling each of said modulation devices so that the projection zones create together said dynamic patterns of light.

In accordance with another aspect of the invention, there is provided a method of influencing the nervous system of a user for recreational purposes by exposing the user to light projections generated by a light modulation system as defined herein using predetermined combinations of control parameters selected to generate visual effects leading to at least one of the following effects: relaxation, stimulation, mood stabilization or balancing. A therapeutic method of treating the nervous system of a patient comprising at least one step wherein the patient is exposed to at least one of such a method of influencing the nervous system is also provided.

In accordance with yet another aspect of the invention, there is further provided a therapeutic method of treating the nervous system of a patient by exposing the patient to light projections generated by a light modulation system as defined herein, using predetermined combinations of control parameters selected to generate stress-reducing visual effects leading to at least one of the following effects: relaxation, stimulation, mood stabilization or balancing.

Other features, advantages and applications of the invention will be better understood upon reading of preferred embodiments thereof with reference to the appended drawings.

BRIEF DESCRIPTION OF THE DRAWINGS

FIG. 1 (PRIOR ART) is a graph illustrating conventional stroboscopic pulsations.

FIG. 2 (PRIOR ART) is a graph illustrating conventional light modulation pulsations.

FIGS. 7A and 7B graphically illustrate the effect of the variation of the phase shift parameter.

FIG. 28 schematically illustrates the field of view of the right and left eyes of a user wearing goggles equipped with a light modulation system according to the present invention.

FIG. 29B is a view of the inside of the projection shell of the chair of FIG. 29A.

Figure 3:
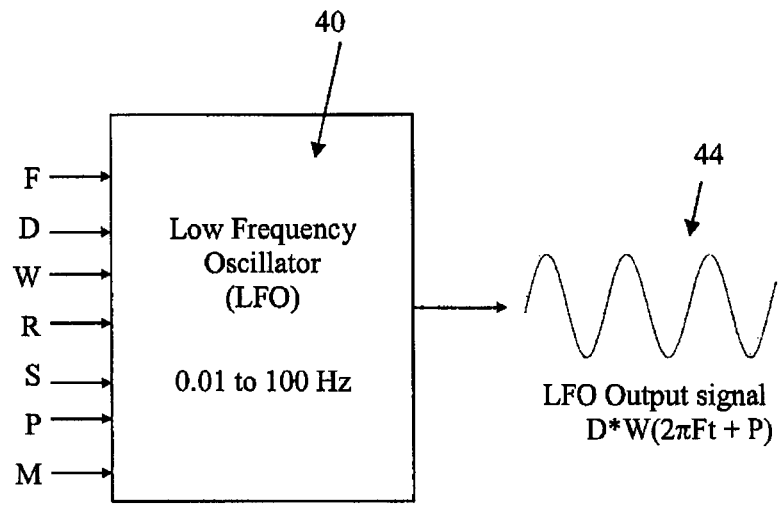
FIG. 3 is a schematic diagram of a basic LFO.

DESCRIPTION OF PREFERRED
EMBODIMENTS OF THE INVENTION

In accordance with various embodiments of the present invention, there are provided light modulation devices for generating modulated color component output signals adapted for use by a light projection device, for modulating light projected thereby. There are also provided light modulation systems including several light projection devices projecting light in different projection zones, arranged to create non-representational dynamic patterns of light.

In the context of the present invention, light modulation is understood to refer to any variation of the intensity or color of the projected light which repeats according to a predetermined pattern. Depending on the target application and desired effect, this modulation can be effected in a lot of different manners.

Light modulation devices and systems according to embodiments of the present invention may for example allow a sophisticated proportional control of light intensity, which can be used to generate subtle pulsing variations. The depth of such pulsing variations can be made so small that the resulting effect is barely perceptible, creating a gentle, shimmering vibration instead of a brain-hammering flicker as is done through stroboscopic pulsations. Such subtle pulsing variations with such reduced depth are also safer to use, since they are much less likely to provoke epileptic reactions. By toning down pulsations until they are barely perceptible, a new mode of interacting with brainwaves can be attained, which can imbue the modulated light with particular qualities related to brainwave frequencies.

Embedding pulsations at such non-invasive levels results into what could be called a "psychoactivation" of light. For example, it has been found that light softly shimmering at frequencies in the Beta range (14-30 Hz) has a zesty wakening quality, fine pulsations in the Alpha range (8-13 Hz) are peaceful and relaxing, while subtle vibrations in the Theta range (4-7 Hz) can intrigue and inspire creativity. Of course, the present invention is not limited to such applications and light modulation having a different effect, or no effect at all, on human perception may also be considered.

In one embodiment, the frequency of the light modulation is within a range of about 1/100 Hz to about 100 Hz. The upper limit of this range is determined by what is known as the flicker fusion frequency: this is the highest frequency that the eye can commonly perceive, above which a pulsing light increasingly looks like an averaged continuous source. Generating higher frequencies can however also be of interest, for purposes other than purely visual effects. LED light sources can for example be driven at frequencies as high as this limit or much higher. The lower limit of this frequency range corresponds to roughly one cycle per minute. Below this, oscillations are so slow that they stop being perceived as a single continuously connected phenomenon. At the center of this range (at about 1 Hz) sits the threshold between what can be called in perceptual terms the frequency and time domains: oscillations above this are perceived as unified vibrations (frequency perception domain), while below they become slow enough for the brain to resolve them into the constituent phases of each cycle (time perception domain). Light Modulation effects of interest may be obtained within the area merging these two domains. However, modulation of light at any desirable frequency is equally considered to be part of the scope of the present invention.

The term "light projection device" is understood to refer to any component, module, system, assembly, or the like which may produce an area of light of varying intensity and/or color. Each light projection device used in the context of the present invention may be embodied by a plurality of projectors, each generating and projecting light of a specific color and superposed so as to create the beam of light of varying intensity or color. Each such projector would therefore receive a specific one of the color component output signals. Alternatively, the different light components of the beam of light could be generated by a single integrated device.

The light projection devices can be realized in a variety of ways: they may for example be incandescent light projectors for large-scale projection areas, LEDs incorporated in goggles, or a miniature screen for small-scale projection areas or in light projectors for large-scale projection areas. The incandescent light projectors and/or LEDs may be controlled by power dimmers responding to the output signals of the light modulation devices. Still other types of light projectors which can be realized include RGB video projectors and LCD screens controlled by a video modulator responding to the outputs signals.

The modulated color component output signals may be embodied by any combination of signals which together control the intensity and color of the light projected by the light projection devices. In one embodiment, the three color component signals are embodied by R(t), G(t) and B(t) signals, corresponding to the primary colors red, green and blue of a typical RGB scheme. Other color combinations could however be considered without departing from the scope of the present invention. For example, more sophisticated Light Modulators can also be made to control four or more primary colors, enabling a more accurate synthesis of a wider range of visible colors. For example, a Light Modulator with the four primary colors Red, Yellow, Green and Blue (RYGB), can generate better colors in the Yellow range. This range is notoriously difficult to reproduce with the usual RGB three-color Light Modulator. In theory, in an RGB system yellow is obtained by combining Red and Green colors. However in practice this often results in a washed out, unsaturated yellow color. In the four-color RYGB Light Modulator, the yellow color range is obtained by turning on mostly the Yellow source, resulting in more saturated colors. Similarly, a violet color component could be used to give a better control of the resulting color in this range, since Violet cannot be properly obtained by mixing available primary colors in an RGB system: while the best approximation is obtained by mixing Blue and Red colors, this in fact yields a Magenta combination rather than true Violet.

Generally speaking, various embodiments of light modulation devices providing such color component output signals creating a modulation of the projected light are disclosed herein. Each of the illustrated light modulation devices includes a light modulator and at least one modulation generator; examples for each of these components will now be described in detail.

Light Modulator

Figure 9:
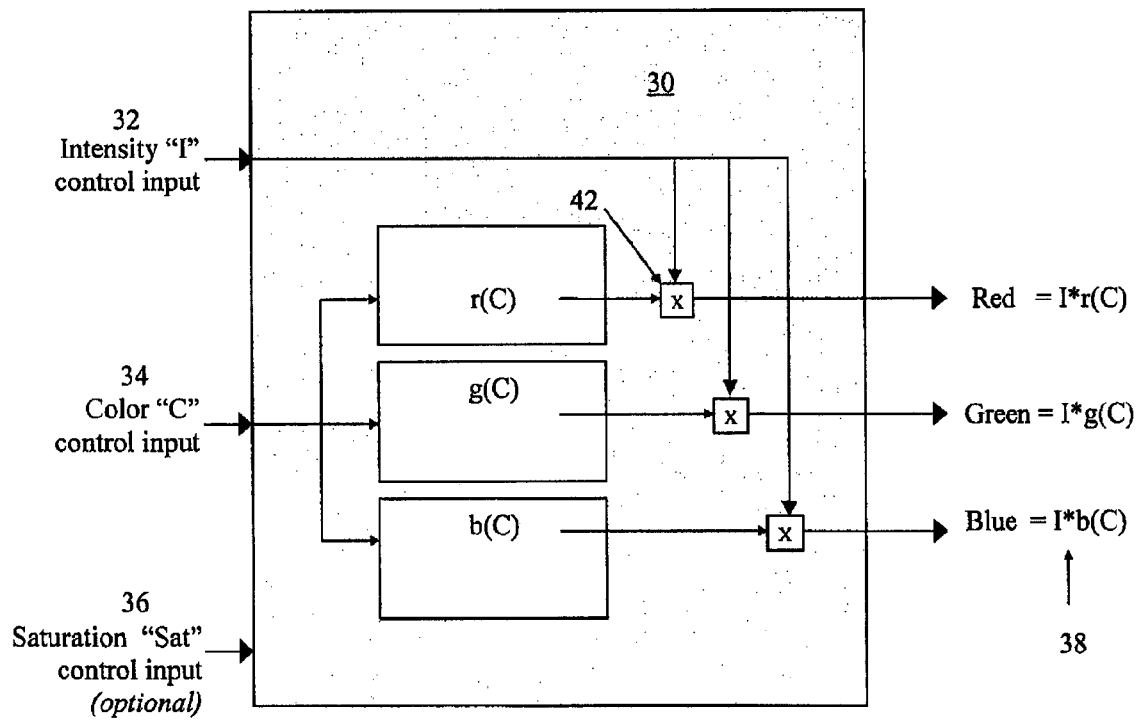
FIG. 9 is a schematic diagram of a light modulator.

Referring to FIG. 9, there is schematically illustrated an example of a light modulator 30. The light modulator 30 combines a light Intensity parameter "I" 32 with a Color parameter "C" 34 and an optional Saturation parameter "Sat" 36 to generate at least three control outputs 38 with intensity signals for primary color projector channels. These 3 input parameters are respectively equivalent to the "Brightness", "Hue" and "Saturation" components of the "HSB Color Model" (also known as "HSV") well known in the art of colorimetry. As will be seen, the Light Modulator essentially performs an operation similar to a translation from HSB to RGB Color Models.

As is well known in the art of colorimetry, when the light generated by primary color channels is combined over the same projection surface in varying proportions, it mixes through the process of additive synthesis and forms a variety of colors ranging within the color gamut bounded by the primary colors. This can for example be visualized with the standard CIE 1931 Chromaticity Diagram representing visible colors, as specified by CIE (Commission Internationale de l'Éclairage, Austria). In typical light projection systems the three primary colors selected are Red, Green and Blue because they match the spectral sensitivity of the three types of cones contained in the retina of our eyes. As mentioned above, other color schemes may however also be considered, as well as the use of a different number of "primary" colors.

Figure 10:
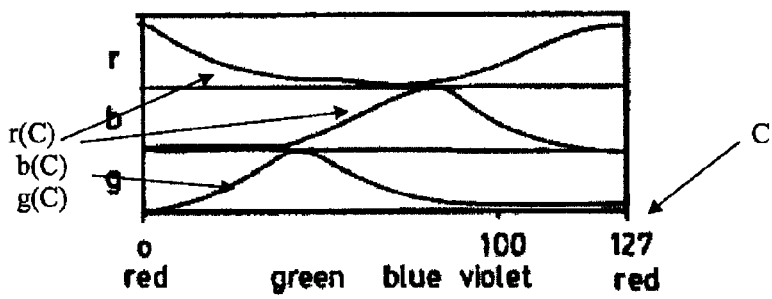
FIG. 10 illustrates the color scaling transfer functions for additive synthesis.

In one embodiment the Light Modulator 30 is designed to generate saturated colors, i.e. pure colors of the rainbow with minimal white content, in which case saturation is assumed to be fixed at its maximum value and the optional Saturation signal "Sat" is not used. The output signals 38 will therefore be determined by the intensity and color parameters. Saturated colors are obtained by using the Color Scaling functions shown in FIG. 10 for each of the three primary colors: r(C) for Red, g(C) for Green and b(C) for Blue, with C being the Color parameter 34. The range of the Color parameter 34, referred to herein as $C_{range}$, is arbitrary; in the following examples we will assume $C_{range}$=128. The range of the Color Scaling functions output is defined as ranging from 0 to 1.

By a visual phenomenon well-known in the art of colorimetry, mixing Red and Blue primary colors in various proportions creates the sensation of a continuous color scale which extends beyond the blue and violet end of the rainbow spectrum, through magenta and back to red, which is the first color at the opposite end of the rainbow. This is referred to as the "Color wheel", since the range of visible colors appears to be smoothly looping in a circle rather than spanning a linear range as in the rainbow, and in the HSB Color Model the Hue signal is given a circular range from 0 to 360°. The Light Modulator 30 may use such a Color Wheel scheme. Table 1 shows an example of three Color Scaling functions defined so that the Color signal C is proportional to the rainbow spectral distribution from Red to Violet (or its Magenta approximation) within the 0 to 100 range for C, and the color range closing the Color Wheel between Magenta and Red is given the Color signal C range 100-128.

In the Light Modulator 30, each of the three outputs of the Color Scaling functions r(C), g(C) and b(C) are multiplied by the Intensity signal value through an appropriate mixing function 42, shown here to be multiplicative by way of example, to obtain the three final color components signals 38 Red, Green and Blue equal respectively to I*r(C), I*g(C) and I*b(C). The range of the Intensity parameter I, which we will call $I_{range}$ is arbitrary; in the examples shown in Table 1 below we will assume $I_{range}$=100.

TABLE 1

| Color Signal "C" value | Red Scaling r(C) | Green Scaling g(C) | Blue Scaling b(C) | Color obtained by mixing Red, Green and Blue components |
|---|---|---|---|---|
| 00 | 100% | 0 | 0 | Red |
| 30 | 50% | 50% | 0 | Yellow |
| 50 | 0 | 100% | 0 | Green |
| 65 | 0 | 50% | 50% | Turquoise |
| 80 | 0 | 0 | 100% | Blue |
| 100 | 50% | 0 | 50% | Magenta |
| 128 | 100% | 0 | 0 | Red |

In applications where the Saturation signal is desirable to generate visual effects with more pastel colors, for example, the Light Modulator 30 may implement a function adding an amount of white mixture, i.e. equal amounts of Red, Green and Blue, inversely proportional to the value of Sat, while scaling down the three r, g, b values to maintain constant overall brightness. The range of the Saturation parameter Sat, $Sat_{range}$ is arbitrary. A value Sat=0 results in white color output with r=g=b independently of the value of C. A value Sat=$Sat_{range}$ results in maximally saturated colors with no white portion added; this is the default condition in embodiments of the present invention where the optional Sat parameter is not implemented.

Modulation Generator

In the illustrated embodiments, each light modulation device includes at least one modulation generator which produces a modulated signal. The modulated signal may be a modulated color signal, provided to the light modulator to control the color parameter, or it may be a modulated intensity signal for controlling the intensity parameter. Either one or both of the color and intensity parameters may be controlled by a modulated signal, provided by a corresponding modulation generator, in a given example of a light modulation device. Several possible non-exhaustive combinations will be described further below.

Each modulation generator includes at least one Low Frequency Oscillator (LFO). The embodiments described with reference to FIG. 14 and following will give examples of how the LFOs may be used alone or in combination to provide light modulation of varying complexity.

Low Frequency Oscillator

FIG. 3 of the appended drawings, illustrates the schematic structure of a LFO 40. Such LFOs are believed to be well known in the art of electronic design and sound synthesis, and as such do not need to be described in detail herein. Their function is to generate a low frequency oscillating signal 44, according to a number of input waveform parameters. The "low" frequency range is typically consider3ed to apply below 100 Hz, although higher frequencies could also be considered within this range if different effects, such as non-visual effects past the flicker fusion, are desired. The LFO 40 is preferably optimized for light modulation purposes, and as such some of its waveform parameters may be used differently than in LFOs common in sound synthesis.

The Frequency parameter "F" sets the running frequency of the oscillator. In one embodiment, the frequency is selected within a range having a minimum of about 0.01 Hz and a maximum of about 100 Hz. For optimal visual effects control, the Frequency parameter will preferably have a logarithmic scale. For example the following scale conversion between the F parameter and the resultant LFO frequency $F_{LFO}$ can be used:

$$F=100+20*\log(F_{LFO})/\log(2) \quad \text{Equation 1}$$

This results in the LFO frequency set at 1 Hz for F=100 and increasing/decreasing one octave per F increment/decrement of twenty, with a range of 1/32 to 32 Hz for F=0 to 200.

The Depth parameter "D" sets the amplitude of the output signal, within a range of 0 to 100% of the nominal operating signal level $I_{nominal}$. If, for example, $I_{nominal}$ is set at 100, the range for D is from 0 to 100. When the LFO is used for Intensity modulation, $I_{nominal}$ may typically be set to the Intensity range $I_{range}$ of the Light Modulator (as described above), and when it is used for Color modulation $I_{nominal}$ will typically be set to the Color range $C_{range}$ of the Light Modulator block (as also described above).

Figure 4:
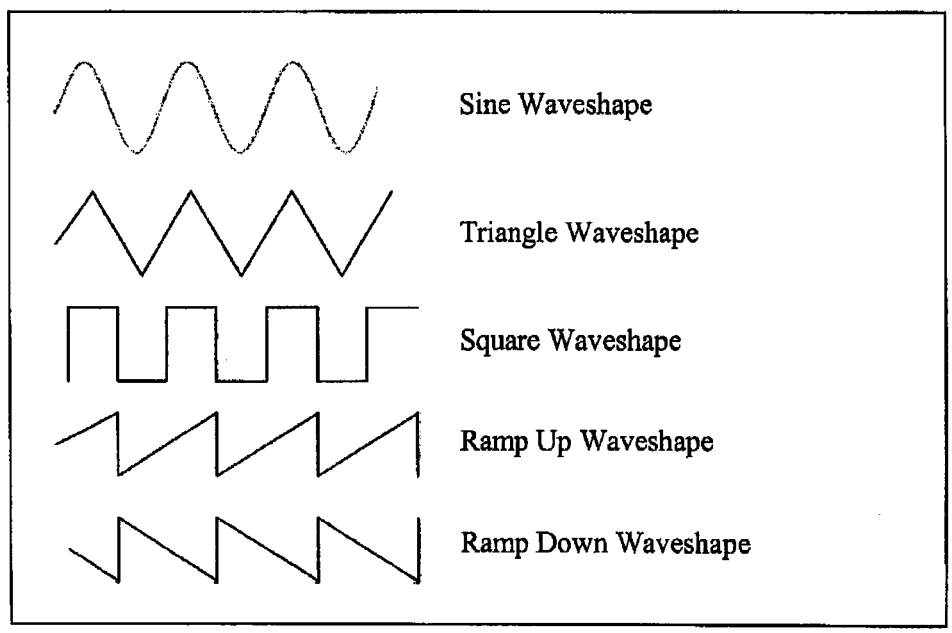
FIG. 4 schematically illustrates typical LFO waveshapes.

The Waveshape parameter "W" selects the shape of the oscillating signal from a variety of possible waveshapes. Non-exhaustive examples of typical LFO waveshapes are shown in FIG. 4: sine wave, triangle wave, square wave, ramp-up wave and ramp-down wave. As will be readily understood by one skilled in the art, other cyclic shapes are also possible, and result in different types of lighting pulsations. The range of W is typically from 1 to the total number of available waveshapes.

Figure 5A:
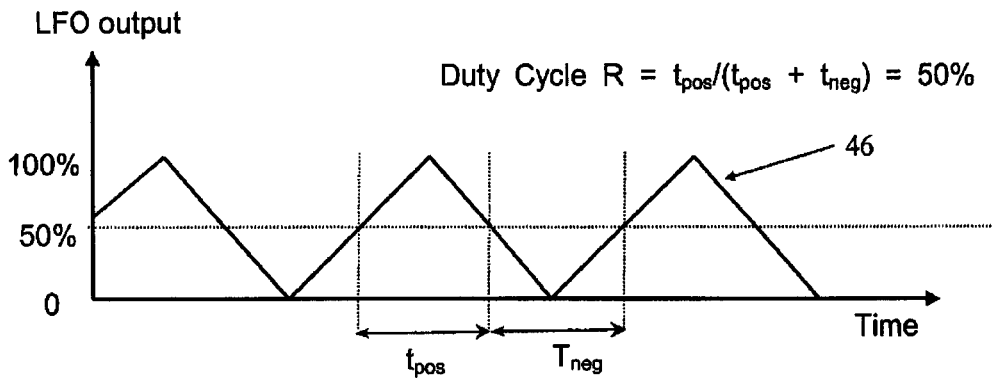
FIGS. 5A to 5C graphically illustrate the effect of the variation of the duty cycle parameter.
Figure 5B:
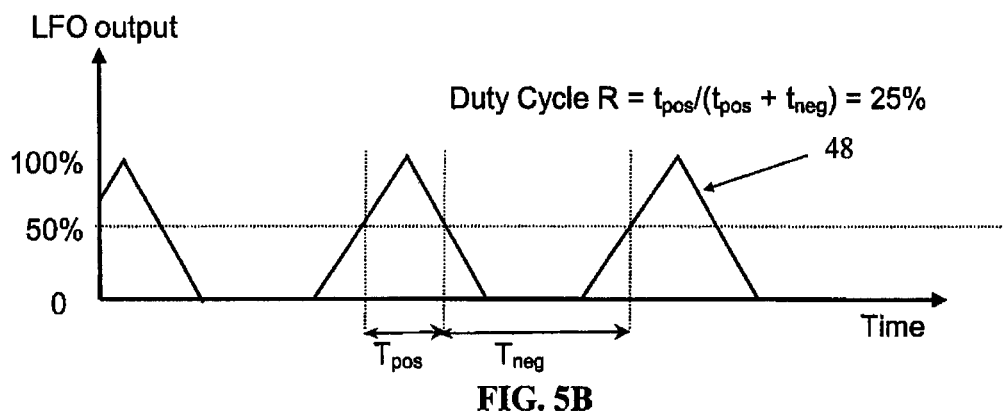
Figure 5C:
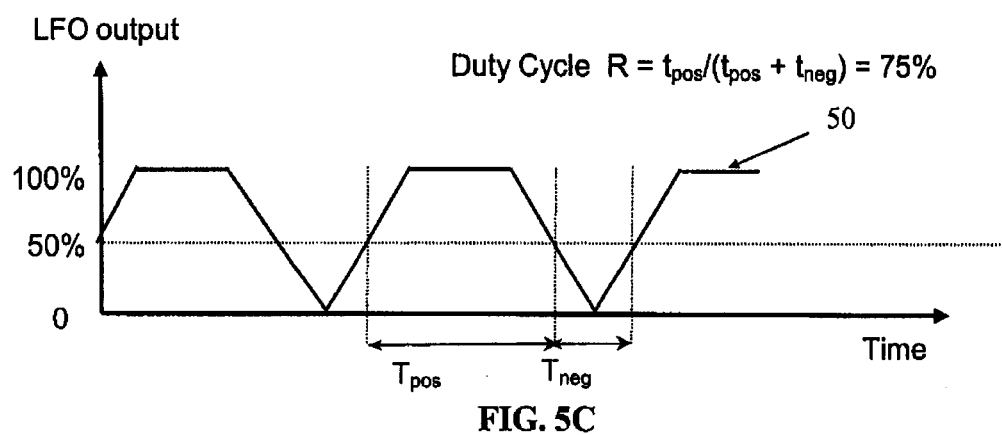

The Duty Cycle parameter "R" sets the duty cycle of the oscillating output signal, as shown in FIGS. 5A to 5C, equal to the ratio of the positive portion of the period "$t_{pos}$" (time spent above the wave midline) versus the negative portion of the period "$t_{neg}$" (time spent below the wave midline) according to the following equation:

$$R=R_{range}*t_{pos}/(t_{pos}+t_{neg}) \quad \text{Equation 2}$$

Where "$R_{range}$" determines the operating range of the parameter, and is typically set to 100. The default normal value for R may be set to 50%, resulting in a symmetrical waveshape 46 as shown in FIG. 5A. Reducing R as in FIG. 5B results in a waveshape 48 compressed between segments at 0% level, while increasing R as in FIG. 5C results in a waveshape 50 compressed between segments at 100% level.

Figure 6A:
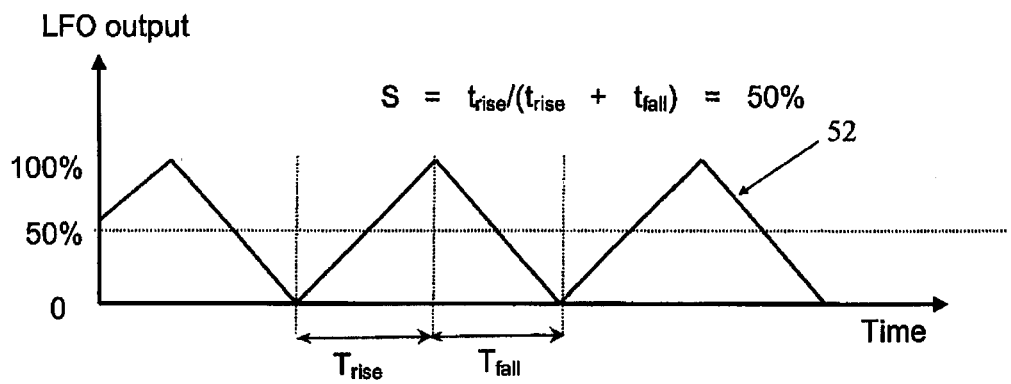
FIGS. 6A to 6C graphically illustrate the effect of the variation of the symmetry parameter.
Figure 6B:
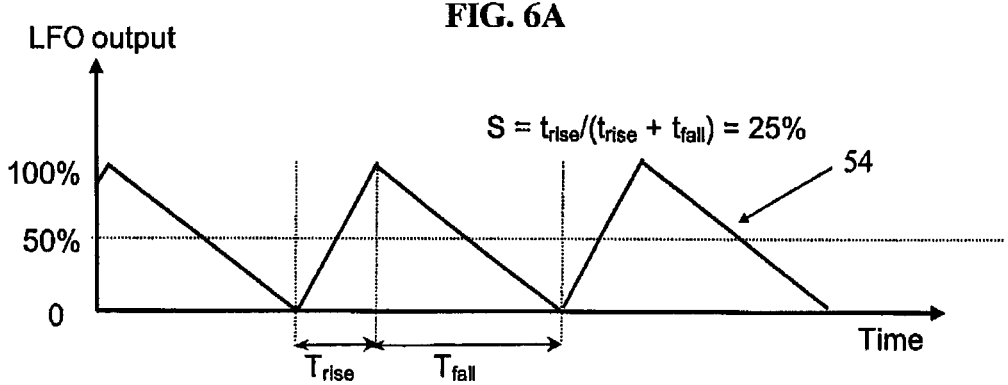
Figure 6C:
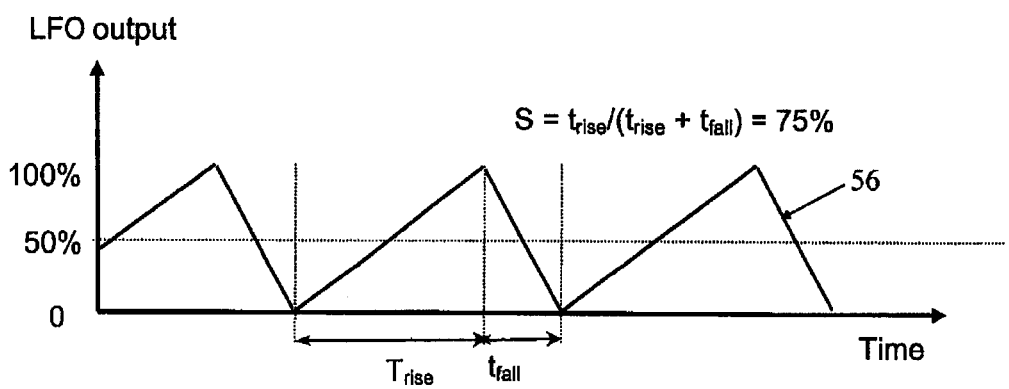

The Symmetry parameter "S" sets the symmetry of the wave cycle as shown in FIGS. 6A to 6C, equal to the ratio of the up-going part of the cycle "$t_{rise}$" versus the down-going part "$t_{fall}$" according to the following equation:

$$S=S_{range}*t_{rise}/(t_{rise}+t_{fall}) \quad \text{Equation 3}$$

Where "$S_{range}$" determines the operating range of the parameter, and is typically set to 100. The default normal value for S may be set to 50%, resulting in a symmetrical waveshape 52, as shown in FIG. 6A. Reducing S as in FIG. 6B results in a waveshape 54 accelerating on the up-going half, while increasing R as in FIG. 6C results in a waveshape 56 accelerating on the down-going half. For waveshapes with $t_{rise}$=0 or $t_{fall}$=0, such as square and ramp waveshapes, the symmetry parameter S is meaningless and is not used. In fact the Ramp Up and Ramp Down waveshapes can be considered special cases of the Triangle waveshape with respectively S=0 and S=100.

The Phase Shift parameter "P" determines the offset time in the starting point of the wave cycle, as shown in FIGS. 7A and 7B. Phase is especially meaningful when many LFOs are working in conjunction at the same frequency: the Phase Shift parameter then determines the time offset between each LFO signal. Phase is traditionally described as having a range "$P_{range}$" from 0° to 360° for a full wave cycle. FIG. 7B shows a wave 60 having the same frequency as wave 58 of FIG. 7A, but shifted in time by a delay "$t_{offset}$". The Phase Shift for this wave is defined as:

$$P = P_{range} * t_{offset} / t_{period} \qquad \text{Equation 4}$$

In FIG. 7B, wave 51 has a $t_{offset} = \frac{1}{4}$ of $t_{period}$ with respect to wave 50 of FIG. 7A, resulting in a phase shift P of ¼=25%, which can also be written as ¼*360°=90°. The range for the P parameter is typically from 0 to 360.

Figure 8A:
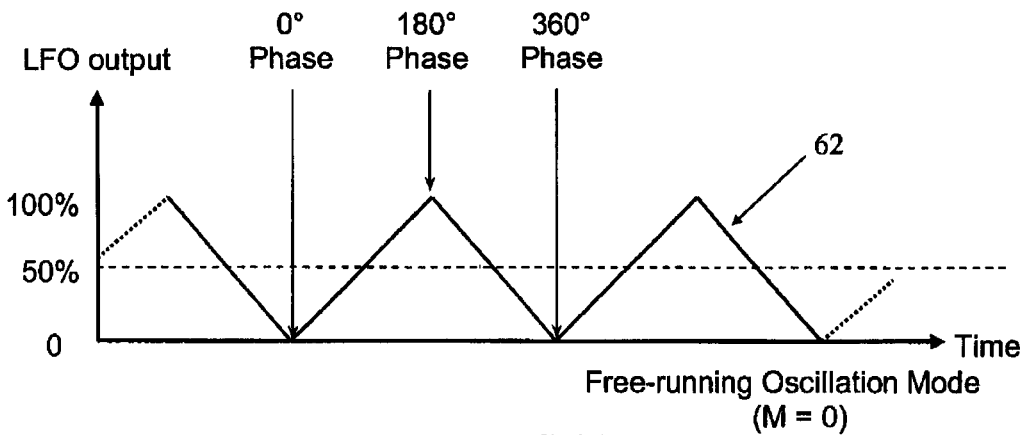
FIGS. 8A to 8C graphically illustrate the effect of the variation of the oscillation mode parameter.
Figure 8B:
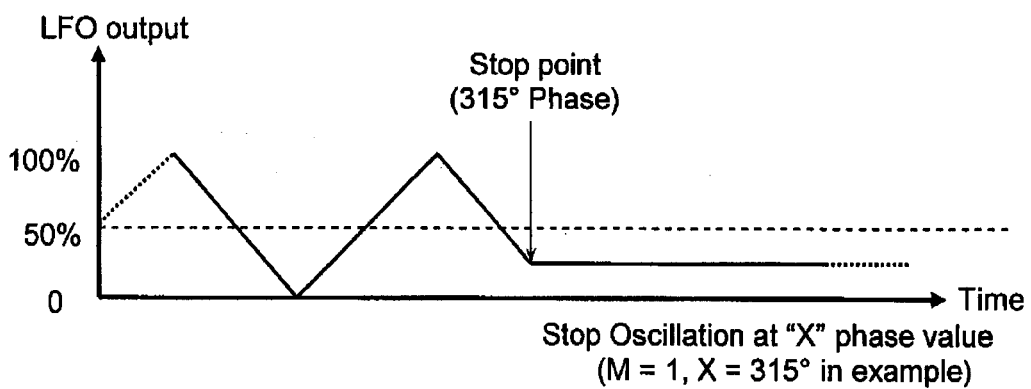
Figure 8C:
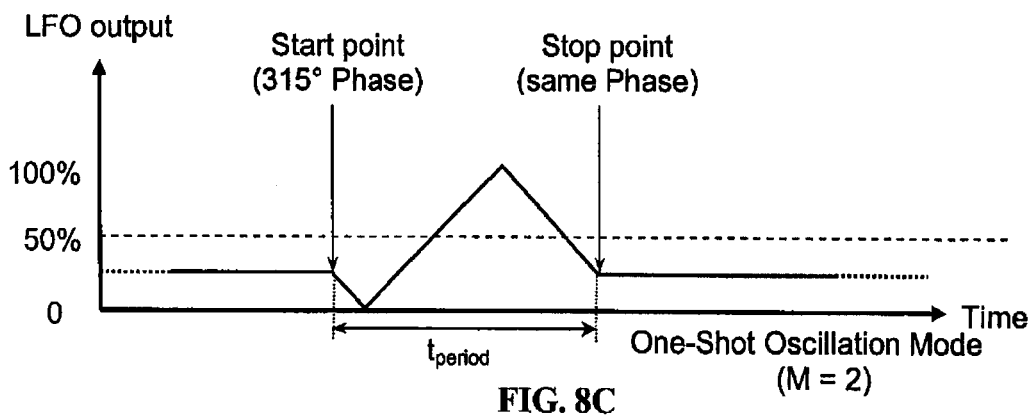

The Oscillation Mode parameter "M" controls the starting and stopping of the LFO's oscillation. The LFO is by default in a free-running mode, i.e. continuously generating its output signal as shown in FIG. 8A wave 62; this mode can be associated with a value M=0. FIG. 8B shows the "Stop Oscillation" mode activated by setting M=1, which allows stopping the oscillation. Once a LFO is stopped, it can be re-started in one of two ways: either by setting M=0 to restore the free-running mode, or by setting M=2 to trigger the "One-Shot" mode, which lets the LFO run for a single full cycle starting from its current phase point, as can be seen from FIG. 8C. Other possible variations on oscillation mode include a "One-Shot" mode with adjustable phase stop point, and a "One-Shot" mode running the LFO for an adjustable portion of a cycle.

It is understood the any parameters above or combination thereof could be used to control the oscillating signal from a LFO in embodiments of the present invention. For example, it has been found advantageous to use LFOs having at least the Frequency and Depth Control parameters described hereinabove. The other parameters can be added to enhance the variety of visual effects generated by the modulation structures. Other combinations are however considered within the scope of the present invention.

In most embodiments, the oscillating signal directly produced by a LFO is not necessarily suitable to be used as the modulated signal controlling either of the intensity or color parameters of the light modulators. The following sections show examples of how a base signal can be used to remedy to this issue.

Combination with Base Signal

Figure 11:
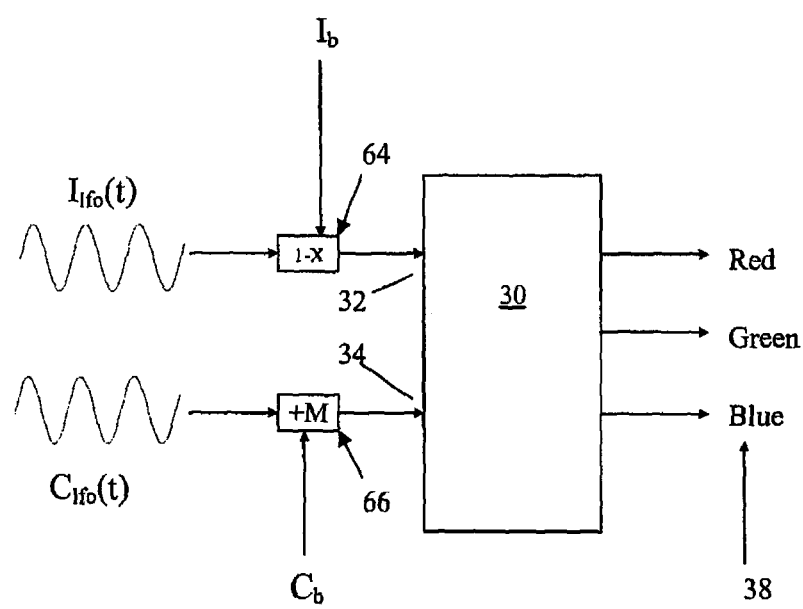
FIG. 11 is a schematic diagram illustrating the combination of LFO oscillating signals with base signals.

As shown in FIG. 11, the light modulation device may use one or both of two main parameters known as the Base Intensity "$I_b$" and the Base Color "$C_b$" which generally define the static base intensity and color of the light projection.

In traditional modulation systems (such as sound synthesizers), parameters are usually combined by simple addition or multiplication. While these methods can be used in the context of the present invention, in one embodiment each type of signal (Intensity and Color) uses a different combination method significantly different from traditional ones in order to optimize the ease of control over visual effects.

The oscillating signal from a given LFO "$I_{lfo}(t)$" may be combined with the Base Intensity signal $I_b$ to provide a modulated intensity signal in the following manner:

$$I_{combined}(t) = I_b * (1 - (I_{lfo}(t)/I_{range})) \qquad \text{Equation 5}$$

This intensity combination operation is for example performed by a multiplicator 64 symbolized schematically by the [1-X] box.

Figure 12A:
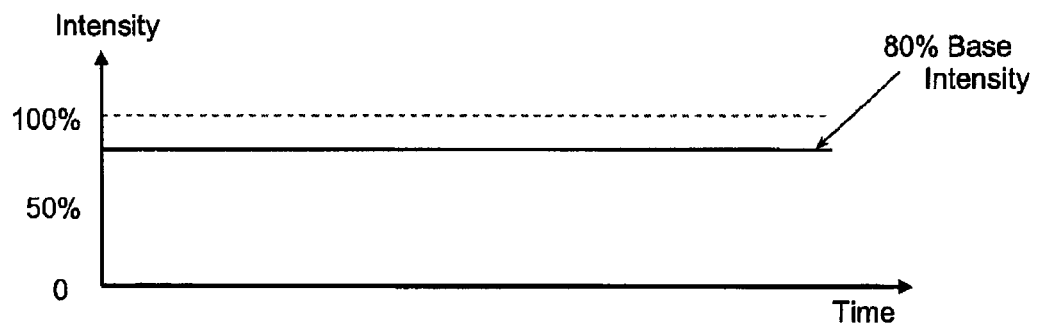
FIGS. 12A to 12C graphically illustrate the results of the combination of a LFO oscillating signal with an intensity base signal.
Figure 12B:
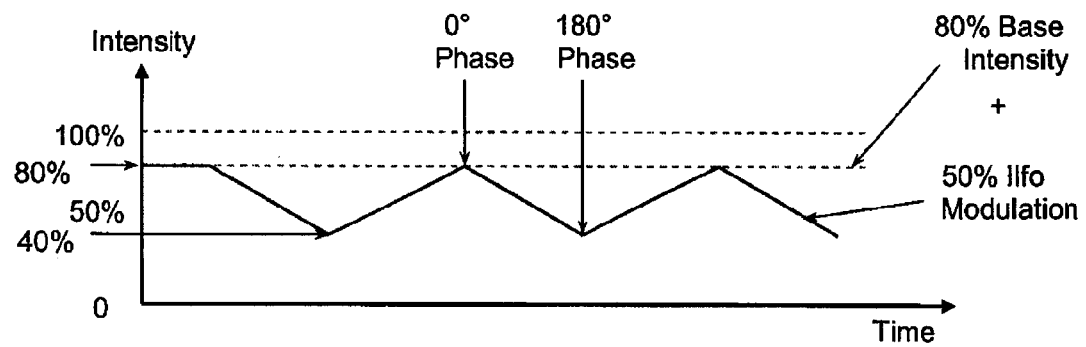
Figure 12C:
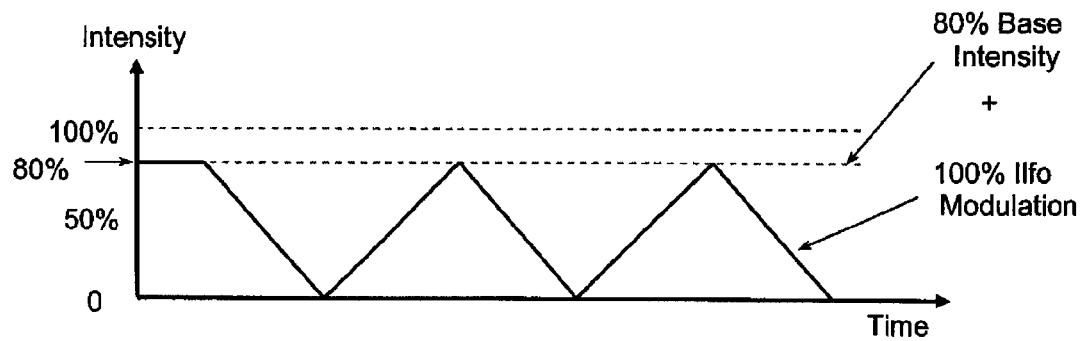

The results of this combination is shown in FIGS. 12A to 12C, with an example starting at FIG. 12A from a static Base Intensity $I_b = 80$ (assuming $I_{range} = 100$).

FIG. 12B shows the modulated Intensity signal obtained ($I_{combined}$) when an oscillating signal $I_{lfo}$ having a triangle waveshape and a Depth range of 50 (therefore varying between output values 0 to 50) is combined with the Base Intensity.

FIG. 12C shows the $I_{combined}$ obtained when an oscillating signal $I_{lfo}$ having a triangular waveshape and a Depth range of 100 (therefore varying between output values 0 to 100) is combined with the Base Intensity.

Advantageously, in such an intensity combination method the LFO Depth parameter directly corresponds to the intensity modulation depth of the resultant light output, with the modulation Depth being automatically scaled with the Base Intensity, and therefore remaining proportionally and visually similar at any Base Intensity value. Furthermore, this combination method eliminates the possibility of clipping the combined Intensity over its maximum range value whatever values are used for $I_b$ and $I_{lfo}$, and however many LFOs are combined together.

Alternatively, the base intensity signal may be time dependent, in which case equation 5 above may be rewritten as:

$$I_{combined}(t) = I_b(t) * (1 - I_{lfo}(t)/I_{range}). \qquad \text{Equation 6}$$

Of course, other combination schemes could be considered, such a summation of the base intensity and the oscillating signal, or a subtraction of the oscillating signal from the base intensity, or a subtraction of one-half the amplitude of the oscillation signal from the summation of the base intensity and the oscillating signal resulting in an intensity oscillation centered around the base intensity. These last combination methods require a clipping of the combined intensity signal to within the light modulator intensity input range [0, $I_{range}$].

Referring back to FIG. 11, in cases where the oscillating signal from LFO "$C_{lfo}(t)$" is to be used to modulate Color, it may be combined with Base Color $C_b$ in the following way:

$$C_{combined}(t) = (C_b + C_{lfo}(t)) \bmod C_{range} \qquad \text{Equation 7}$$

where the "modulo" mathematical operator iteratively removes $C_{range}$ from the summed value until the resultant value falls within the range from 0 to $C_{range}$. This combination method is directly related to the circular property of the Color Wheel: when the summation of two colors exceeds the color range, it simply falls back on a further rotation on the wheel. This color combination operation is for example performed by a modulo summation element 66 symbolized schematically by the [+M] box.

Figure 13A:
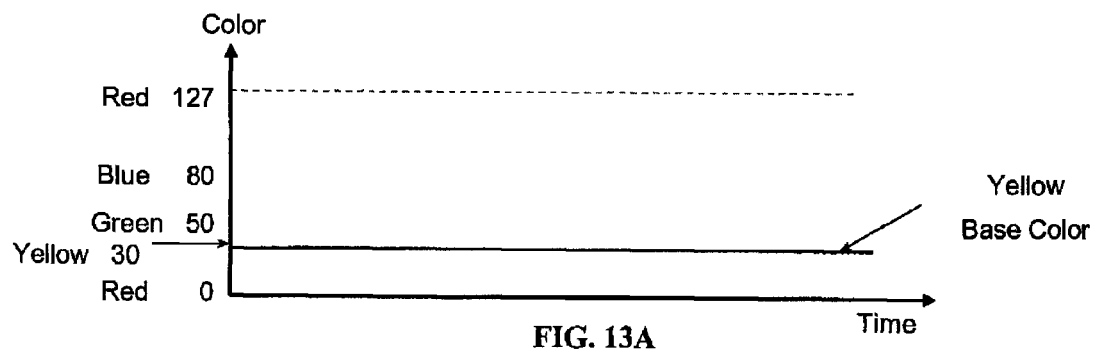
FIGS. 13A to 13C graphically illustrate the results of the combination of a LFO oscillating signal with a color base signal.
Figure 13B:
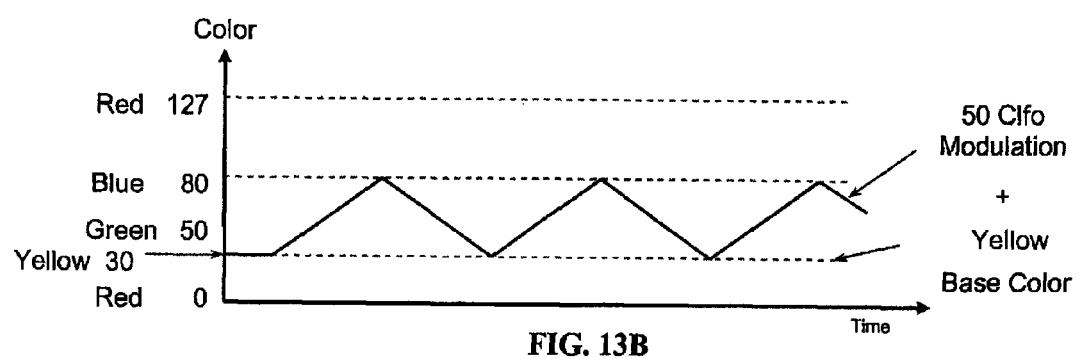
Figure 13C:
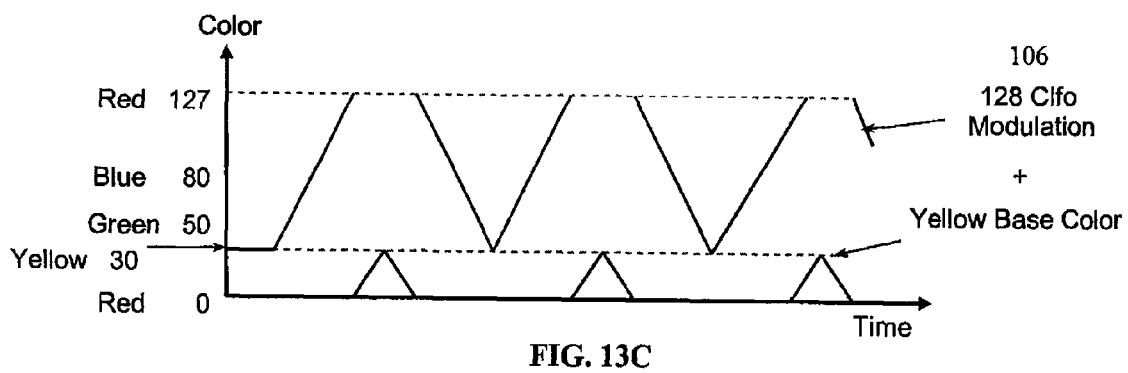

The results of this combination is shown in FIGS. 13A to 13C, with an example starting from a static Base Color $C_b = 30$ shown in FIG. 13A (corresponding to yellow assuming $C_{range} = 128$).

FIG. 13B shows the Color signal obtained when a modulated color signal $C_{lfo}$ having a triangular waveshape and a Depth range of 50 is combined with the Base Color. As can be seen from FIG. 13B, the color oscillates between yellow and blue.

FIG. 13C shows the modulated Color signal obtained when an oscillating signal $C_{lfo}$ having a triangular waveshape and a full Depth range of 128 is combined with the Base Color. As can be seen from FIG. 13, the color going from yellow all the way to red and folding back towards yellow through the modulo operation, effectively sweeping through a full rotation of the color wheel.

The color combination method described above allows the LFO Depth parameter to directly correspond to the range of the color sweep for all values of the Base Color. Furthermore, this combination method eliminates the possibility of clipping the combined Color value over its maximum range value whatever values are used for Cb and Clfo, and however many LFOs are combined together.

Alternatively, the base color signal may be time dependent, in which case equation 7 above may be rewritten as:

$$C_{combined}(t)=(C_b(t)+C_{lfo}(t)) \text{ modulo } C_{range}. \quad \text{Equation 8}$$

Of course, other combination schemes could be considered, such as the modulo subtraction of the oscillating signal from the base color, or the modulo subtraction of one-half the amplitude of the oscillating signal from the modulo summation of the base color and the oscillating signal resulting in a color oscillation centered around the base color. Still other mixing schemes include the simple addition of the base color and the oscillating signal, or the simple subtraction of the oscillating signal from the base color, without the modulo operation; in these last cases the combined color value is clipped within the light modulator color input range [0, $C_{range}$].

Examples of Light Modulation Devices

Light modulation devices according to various embodiments of the invention will now be described in further detail.

Figure 14:
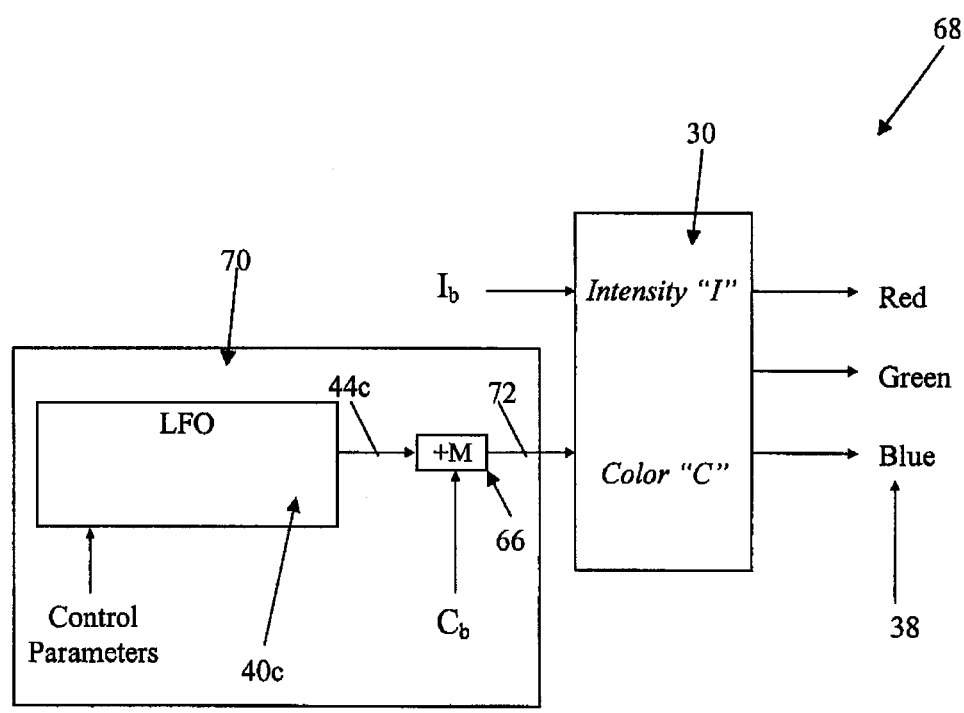
FIG. 14 is a schematic block diagram of a light modulation device according to a first embodiment of the present invention.

FIG. 14 schematically illustrates a light modulation device 68 according to a first illustrative embodiment of the present invention. The light modulation device 68 includes a light modulator 30 which generates the color component output signals 38 according to the intensity parameter "I" and the color parameter "C". In this particular case, the Intensity parameter "I" is set to the base intensity $I_b$, while the color parameter is controlled by a modulated color signal 72.

The light modulation device 68 includes one modulation generator, which is a color modulation generator 70 for generating the modulated color signal 72. The color modulation generator 70 includes a main Low Frequency Oscillator (LEO) 40c generating an oscillating signal 44c, as well as mixing means for mixing this oscillating signal 44c with a base color signal $C_b$, resulting in the modulated color signal 72. The mixing means may include a modulo summation element 66 as explained above, the modulo summation element 66 performing the operation of either equation 7 or 8. Of course, other mixing schemes could be considered as for example described above.

This structure allows the creation of visual effects having dynamic color sweeps controlled by a few simple settings of the parameters of the main LFO.

Figure 15:
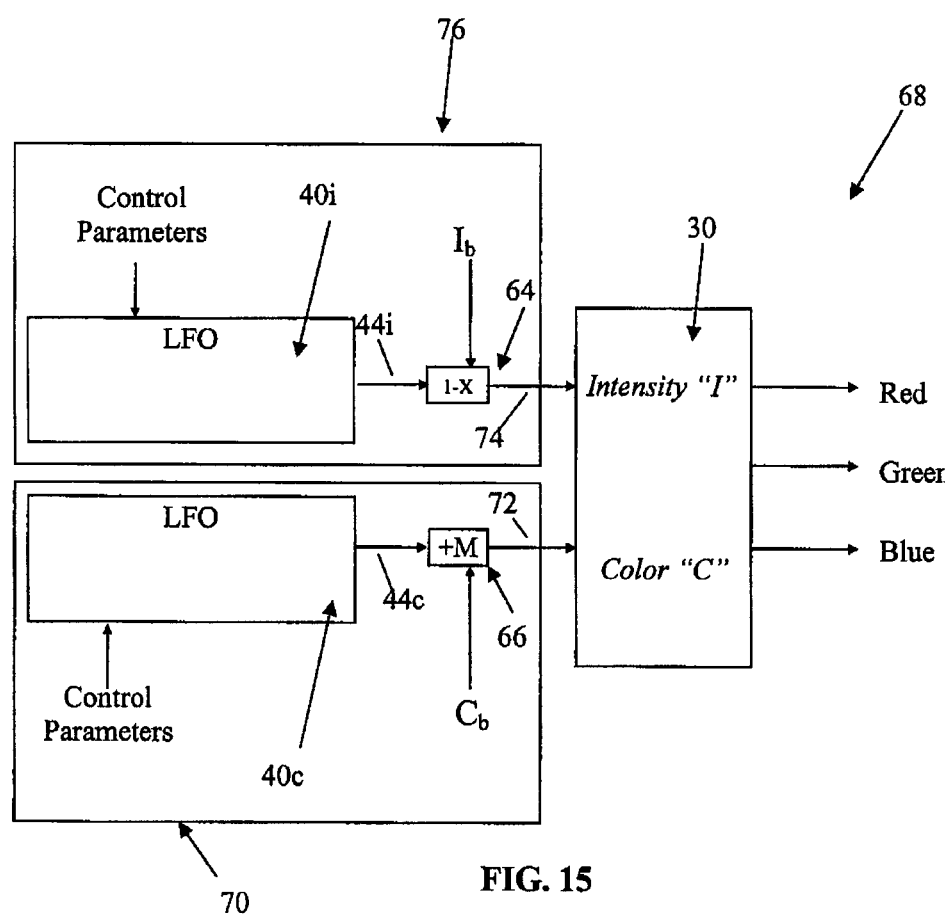
FIG. 15 is a schematic block diagram of a light modulation device according to a second embodiment of the present invention.

Referring to FIG. 15, there is shown a light modulation device 68 according to a second embodiment of the invention differing from the first embodiment of FIG. 14 in that the intensity parameter "I" is controlled by a modulated intensity signal 74. The light modulation device 68 therefore includes an intensity modulation generator 76, in communication with the light modulator 30, for generating the modulated intensity signal 74. The intensity modulation generator 76 also has a main Low Frequency Oscillator (LFO) 40i generating an oscillating signal 44i, and mixing means for mixing this oscillating signal 44i with the base intensity signal $I_b$ in order to obtain the modulated intensity signal 74. The mixing means may include a multiplicator 64 performing the operation of equation 5 or 6, or may alternatively be embodied by other mixing methods such as a summation of the base intensity and the oscillating signal, or a subtraction of the oscillating signal from the base intensity This structure allows the creation of visual effects dynamically combining intensity and color pulsations.

In accordance with another aspect of the invention, a complex modulation of either the intensity parameter, color parameter or both can be used to obtain a different modulation of the resulting light. Embodiments of light projection device having this feature include a complex modulation generator, which includes a plurality, i.e. two or more LFOs. Each LFO generates an oscillating signal, and the oscillating signals are combined to obtain a complex modulated signal. The oscillating signals may be combined in a multitude of fashions, and examples of such combinations are shown in the embodiments described below.

In some embodiments, a complex modulation of the intensity and/or color parameters can be used to combine simultaneous slow and fast modulations. Two LFOs can for example be given distinct predetermined frequencies selected in a proper range for this purpose. Two different but equally interesting types of visual effects are obtained when modulating light intensity or color at the lower LFO frequency range (i.e. roughly between 0.01 Hz and 1 Hz) and higher LFO frequency range (i.e. roughly 1 Hz to 100 Hz). The lower frequency range results in slow, smooth light sweeps that can have an uncannily "organic" feel useful for ambiance effects. The higher frequency range allows light effects interfacing with brainwaves. When using a single LFO for either intensity or color modulations, it is only possible to work within one of these ranges at any given time. Therefore other illustrative embodiments of the invention combine two LFOs for either intensity or color modulation functions or both. This allows the simultaneous integration of both types of light effects, with faster brainwave frequencies superimposed on slow sweeping variations. This capability greatly expands the impact of visual effects generated through the light modulation process. While in principle two such combined LFOs can each operate through their whole frequency range of 0.01-100 Hz, in practice the best light effects are usually obtained by restricting one LFO to the lower frequency range and the second to the higher (brainwaves) range.

Figure 16:
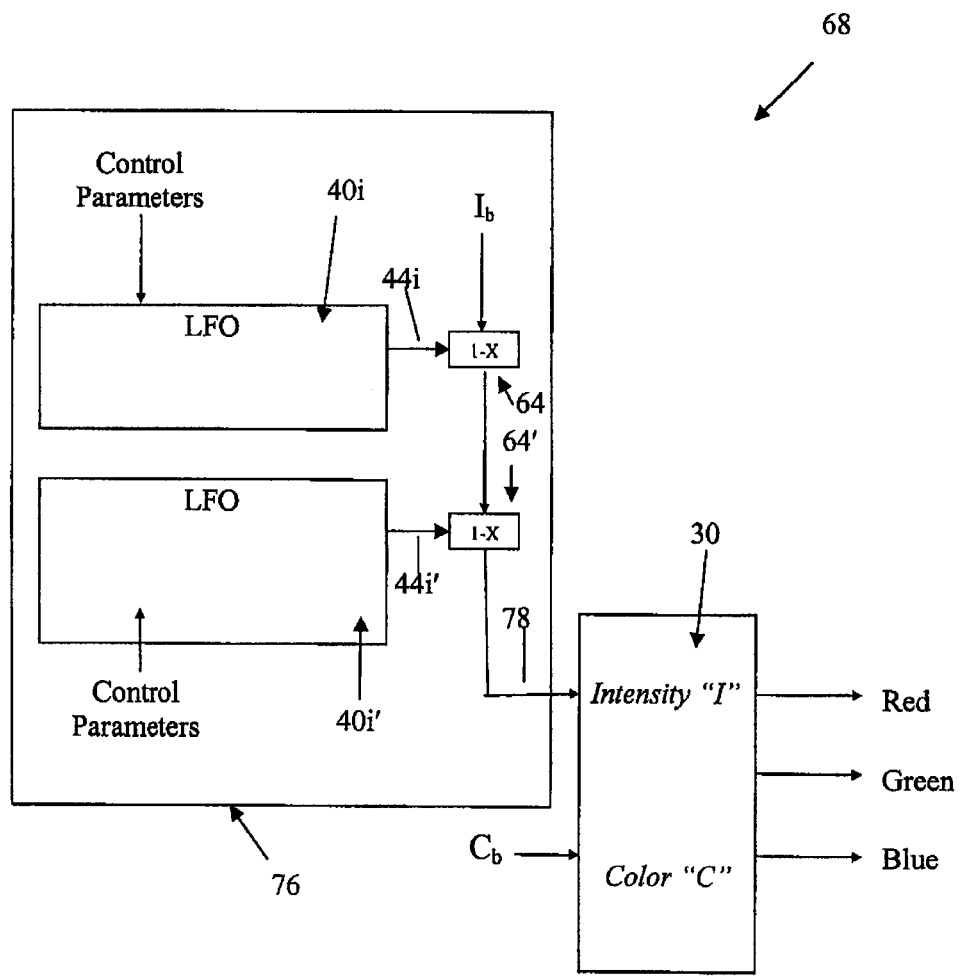
FIG. 16 is a schematic block diagram of a light modulation device according to a third embodiment of the present invention.
Figure 17A:
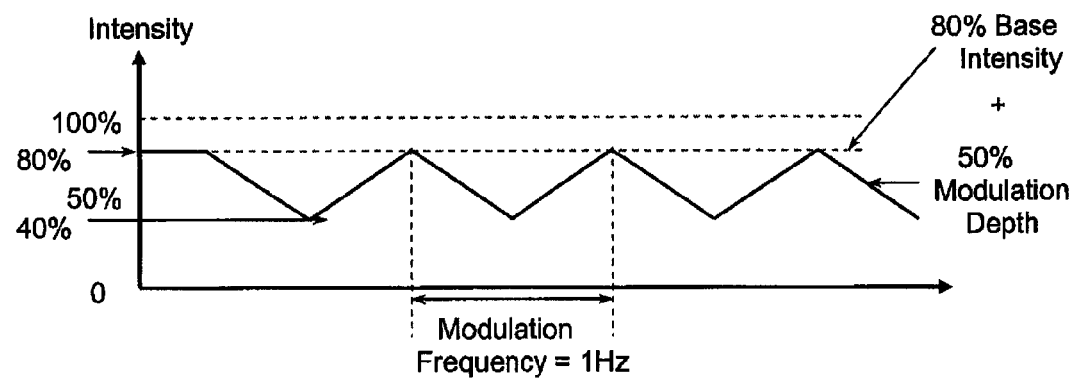
FIGS. 17A to 17C graphically illustrate the respective oscillating signals from the two LFOs of FIG. 16, and the resulting modulated intensity signal.
Figure 17B:
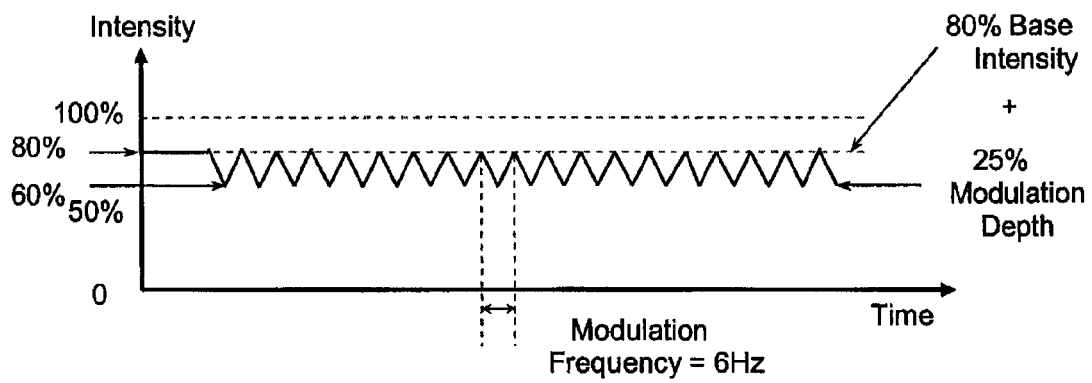
Figure 17C:
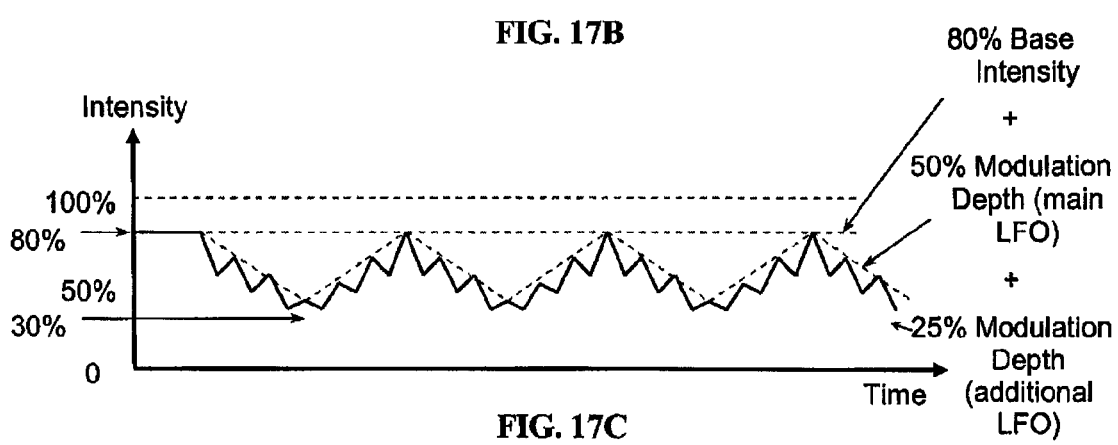

Referring to FIG. 16, there is shown a third embodiment of the invention where the intensity parameter "I" is controlled by a complex modulated intensity signal 78. The color parameter "C" is here set to the base color signal $C_b$. The complex modulated intensity signal 78 is generated by an intensity modulation generator 76 which includes a main LFO 40i generating an oscillating signal 44i, which is mixed with the Base Intensity signal $I_b$ by a multiplicator 64 as above or other mixing means. The resulting modulated signal is then combined with an additional oscillating signal 44i' from an additional LFO 40i'. Another multiplicator 64' is used to mix the two, although again other mixing means could be used such as the direct summation of the two oscillating signals, or their direct multiplication followed by rescaling or clipping to maintain the resultant intensity signal within the light modulator intensity input range [0, $I_{range}$] In the illustrated example, the main LFO 40i is used to generate a slow modulation (sweep effects), whereas the additional LFO 40i' stimulates fast Intensity modulations (brainwave effects), although the reverse could be used. An example of the modulated Intensity signals obtained with this structure is shown in FIGS. 17A to 17C. The modulation from LFO alone is seen at FIG. 17A, the modulation from the additional LFO alone is seen at FIG. 17B, and the complex modulated intensity signal is seen at FIG. 17C.

Although not illustrated, in an alternative embodiment, the color parameter only could be controlled by a complex modulated color signal combining oscillating signals from a main and an additional LFO, respectively generating slow and fast color modulations, with the intensity being set to the base intensity signal.

Figure 18:
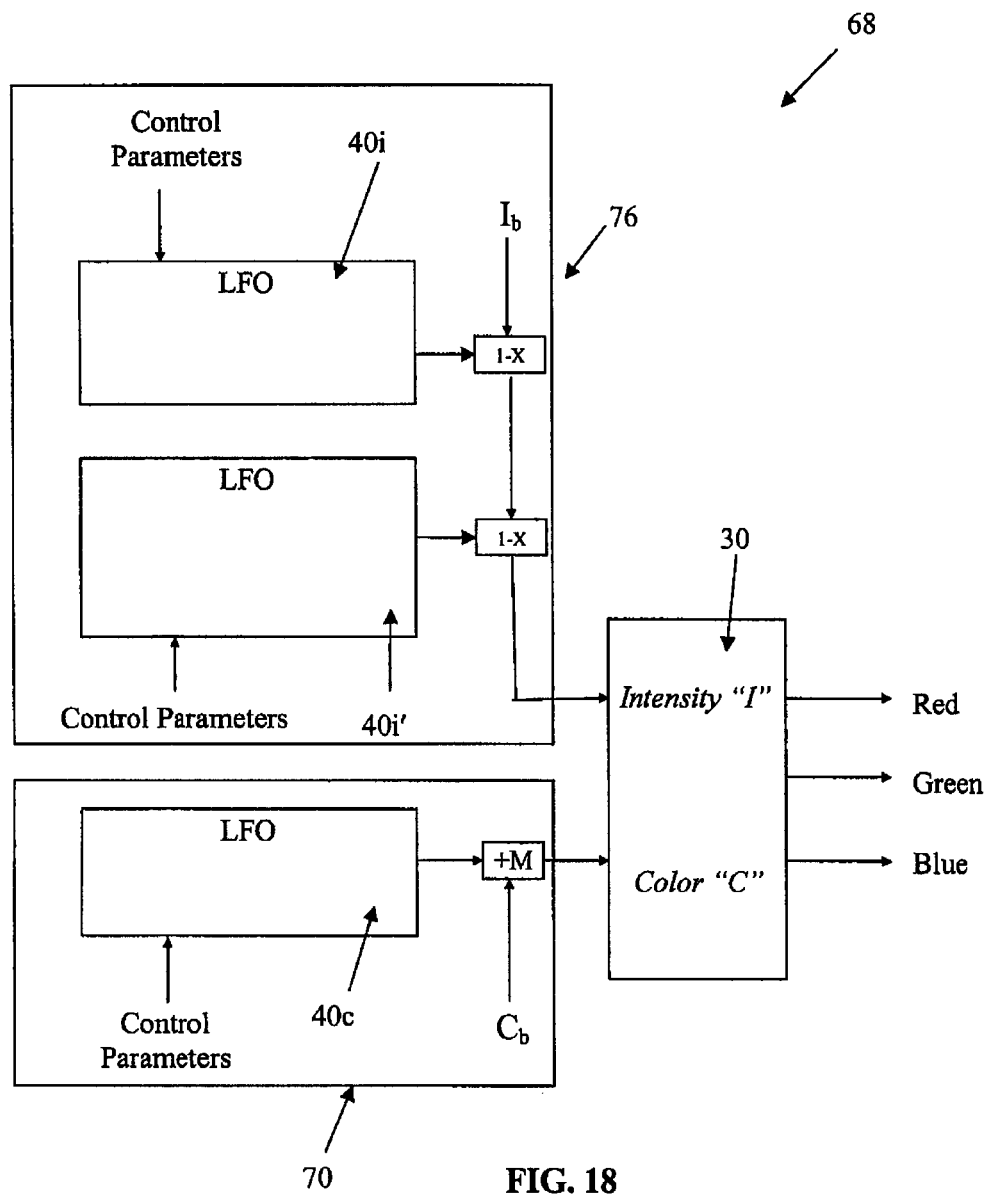
FIG. 18 is a schematic block diagram of a light modulation device according to a fourth embodiment of the present invention.

FIG. 18 shows a light modulation device 68 using three LFOs according to a fourth illustrative embodiment of the present invention. Two Intensity modulation LFOs 40*i* and 40*i'* are combined together and with a Base Intensity $I_b$, forming a complex intensity modulation generator 76, and one Color Modulation LFO 40*c* is combined with Base Color $C_b$, forming a simple color modulation generator 70. This structure allows the integration of Color modulation with simultaneous slow (sweep effects) and fast (brainwave effects) Intensity modulations.

Figure 19:
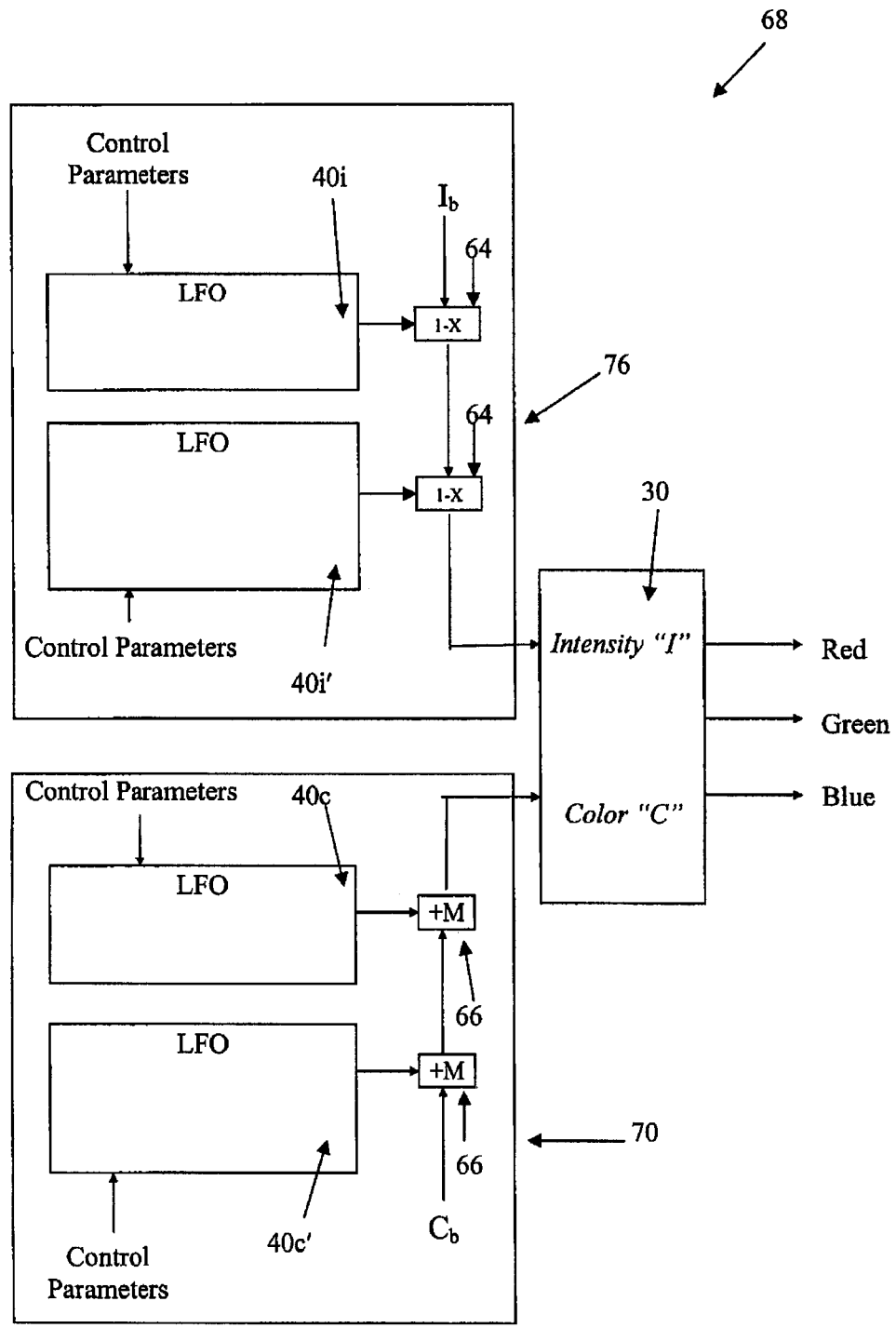
FIG. 19 is a schematic block diagram of a light modulation device according to a fifth embodiment of the present invention.

FIG. 19 shows a light modulation device 68 according to a fifth illustrative embodiment of the present invention using four LFOs. Two Intensity modulation LFOs 40*i* and 40*i'* are combined together and with a Base Intensity $I_b$, and two Color modulation LFOs 40*c* and 40*c'* are combined together and with a Base Color $C_b$ according to mixing means which may include a modulo summation 66 as explained above, the modulo summation element performing the operation of either equation 7 or 8. Of course, other mixing schemes could be considered as described above. This structure adds further flexibility by allowing simultaneous slow (sweep effects) and fast (brainwave effects) modulations of both Color and Intensity.

In the embodiments of light modulation devices described hereinabove, the LFOs of the modulation generators have continuously variable waveform parameters, that is, Frequency "F", Depth "D", Duty Cycle "R", Symmetry "S" and Phase Shift "P" shown in FIG. 3 normally fixed or slowly variable via external controllers so that the resultant light pattern gradually evolves.

A new class of visual effects can be obtained by generating one or more input parameters themselves from an additional layer of LFOs. In such embodiments, the complex modulation generator may include a main LFO generating the main oscillation signal and at least one control LFO, each operatively connected to the main LFO for controlling a corresponding waveform parameter thereof. The combination of the main LFO and associated control LFO is referred to as a modulation set.

Figure 20:
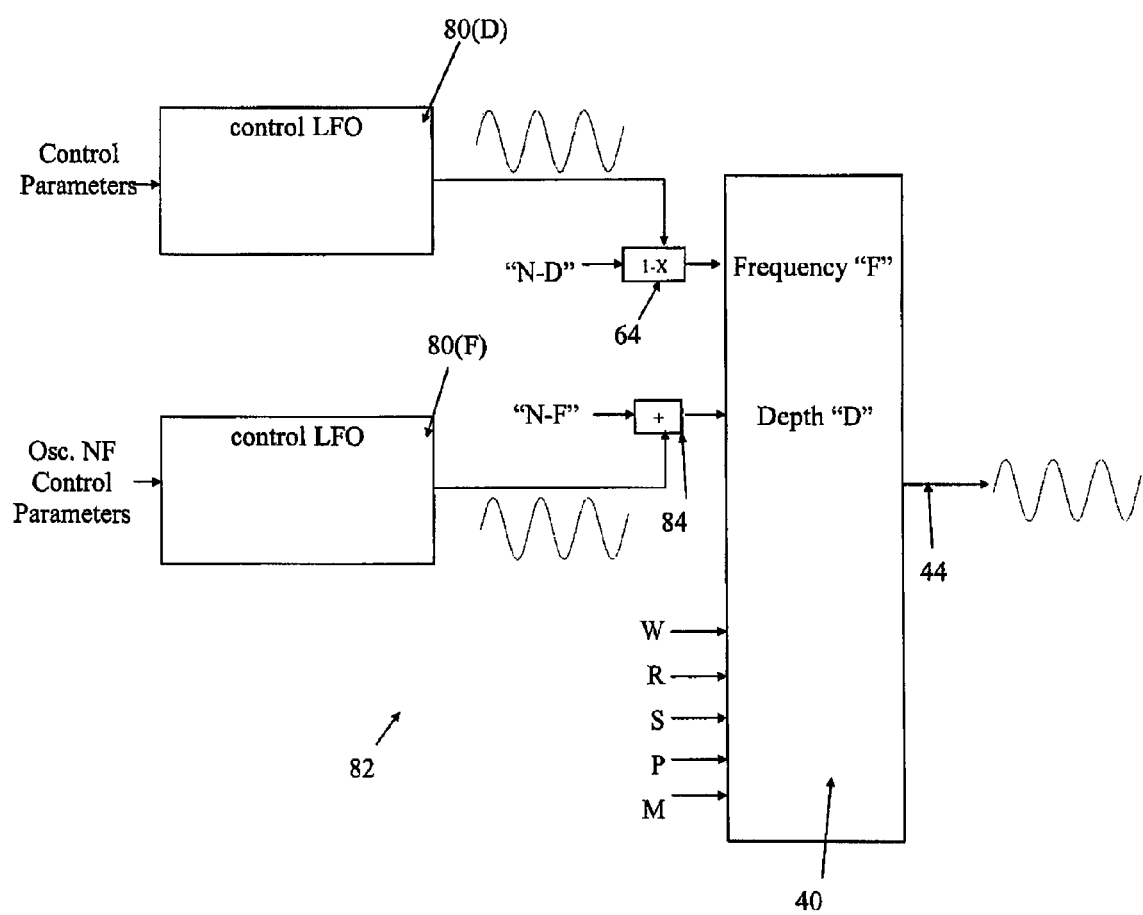
FIG. 20 is a schematic block diagram illustrating a modulation set made-up of three LFOs.

An example is shown in FIG. 20, where the two waveform parameters Frequency "F" and Depth "D" are each controlled by a dedicated control LFO 80. In this recursive structure, the main LFO 40, for example one of the LFOs of FIG. 19, is replaced by a modulation set 82 of three LFOs: the main LFO 40, and the two control LFOs 80(D) and 80(F) performing amplitude and frequency modulation on the main LFO 40.

The output signal from the control LFO 80(D) associated with the depth parameter is combined with a Set Base Depth "N-D" (which replaces the Depth parameter "D" of the main LFO) by a multiplicator 64 or other appropriate mixing means, and the combined signal becomes the Depth parameter "D" for the main LFO 40. This in effect results in amplitude modulation of the oscillating signal 44 from the main LFO 40.

The output signal from the control LFO 80(F) associated with the frequency parameter is combined with a Set Base Frequency "N-F" (which replaces the Frequency parameter "F" of the main LFO) by appropriate mixing means, for example a sum element 84, and the combined signal becomes the Frequency parameter for the main LFO 40. This in effect results in frequency modulation of the oscillating signal 44 from the main LFO 40.

Controlling parameters "F" and "D" with dedicated LFOs typically yields interesting visual effects. However, other types of visual effects can be obtained by adding new dedicated control LFOs to control the other parameters of the main LFO having a continuous input range, namely parameters Duty Cycle "R", Symmetry "S" and Phase Shift "P". It will be understood by one skilled in the art that in a given light modulation device any one, two or more of these waveform parameters could be controlled through the oscillating signal of control LFOs. The oscillating signal from the control LFO may be used as generated or be transformed before being inputted in the main LFO. In one alternative, an oscillating signal from one control LFO may be split and used to control more than one waveform parameter of the main LFO. A great number of variations could be devised, provided enhanced light modulation capabilities and flexibility.

A modulation set of this type can be used to replace any, some, or all of the LFOs of the previous embodiments. One skilled in the art will understand that a variety of combinations can be considered. Modulation sets may be used in a complex color modulation generator, a complex intensity modulation generator, or both. If such a complex modulation generator is used for only one of the intensity and color parameter, the other such parameter could for example be controlled by a simple modulation generator, using a single LFO, or by a base intensity or color signal, which can be fixed or time dependent. A complex modulation generator could combine more than one modulation sets, for example in a pair dedicated to slow and fast frequency modulations, or alternatively combine a modulation set with a simple LFO.

Figure 21:
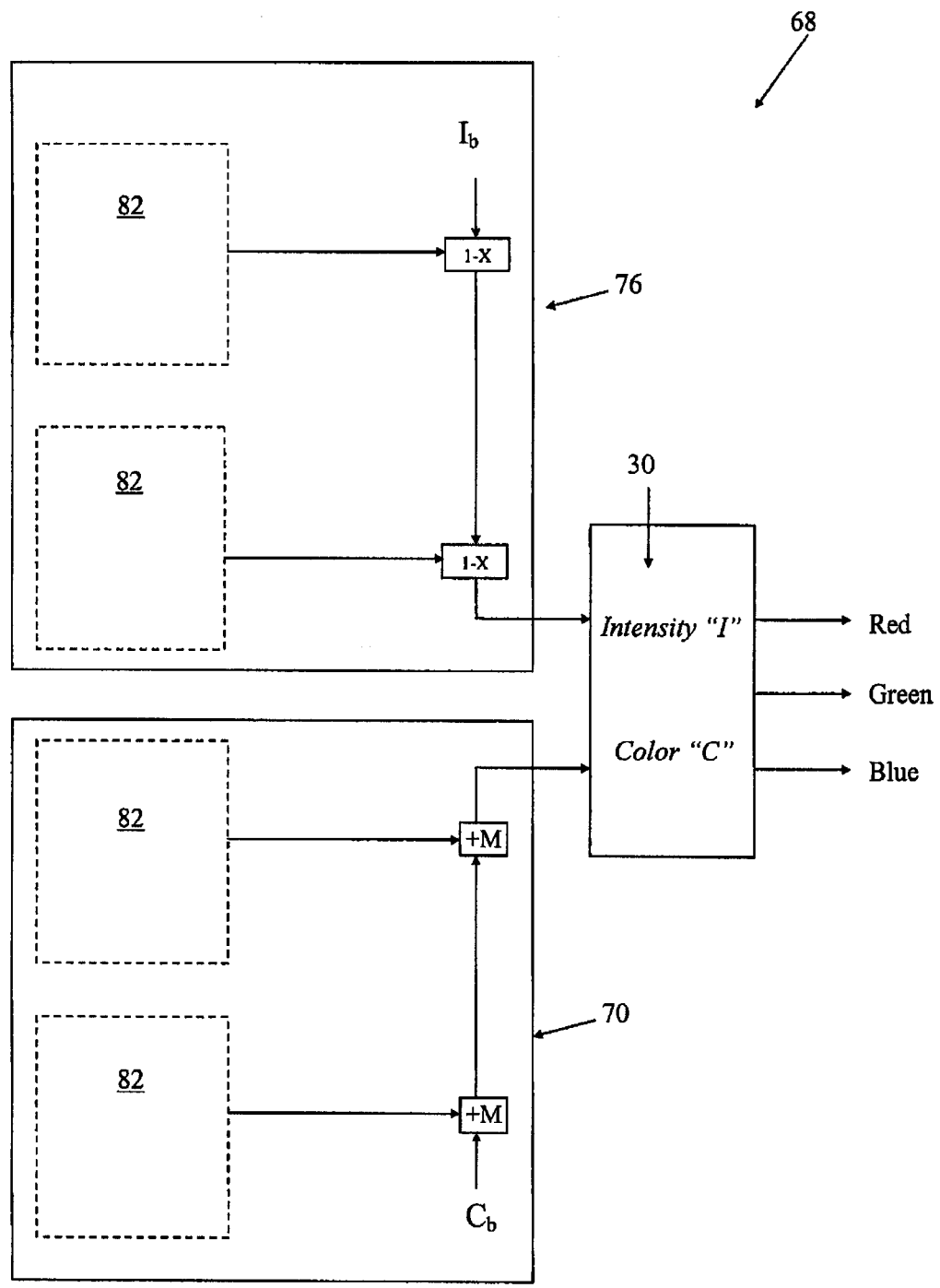
FIG. 21 is a schematic block diagram of a light modulation device according to a sixth embodiment of the present invention.

An example of the enhanced version of the four LFOs structure shown in FIG. 19 is illustrated in FIG. 21. This figure therefore illustrates a light modulation device 68 according to a sixth illustrative embodiment of the present invention. In the third device 68, each of the original LFO is replaced with a three LFOs Modulation Set 82 similar to that shown in FIG. 20, for a total of twelve LFOs in the complete light modulation structure. Such a structure is a powerful tool to generate sophisticated and complex visual effects in a way previously inaccessible.

It is to be noted that while triangular shape waveforms have been used for illustration in the appended drawings, other waveshape signals, such as the waveshape signals illustrated in FIG. 4 for example, could be used.

As one skilled in the art will readily understand, the various constituents of the light modulation devices according to embodiments of the invention may in practice be realised by any appropriate component. In an all digital embodiment, the light modulation device may for example be integrated in a processor provided with appropriate software. Analog embodiments, where appropriate circuit elements enable the signal generation and processing of the light modulation device may also be considered, as well as combinations of digital and analog components. The light modulation device may be embodied within a single stand-alone device, or by separate components in communication with each other. In another variant, the light modulation device may be integral to the light projection device it provides the color component output signals to. It is further to be noted that the color component output signals may be outputted separately or in a multiplexed fashion, using a variety of communication and control protocols, ranging from individual analog proportional intensity controls to multiplexed digital protocols such as the lighting industry standard DMX-512. The color component output signals will often control power dimmers, which will in turn drive the light projection devices since their power may vary from a fragment of a watt (eg. In the case of small LEDs) to thousands of watts or more (eg. for large incandescent projectors) depending on the light modulation system implementation.

Alternatively, the light modulation device may work in parallel with standard light-control consoles as currently used for stage lighting, or may even be integrated within variants of such light-control consoles, enabling the combination of novel light modulation special effects with more traditional, scene-based stage lighting control as supplied by standard consoles.

In common embodiments, the light modulation device will consist of an electronic circuit assembled from analog integrated circuits (in the case of an analog embodiment) and/or digital integrated circuits (in the case of a digital embodiment) soldered on a printed circuit board, with inputs for light modulation control signals and outputs for the control of the light projector color components.

Light Modulation System

In accordance with yet another aspect of the present invention, there is also provided a light modulation system for creating non-representational dynamic patterns of light.

The system includes a plurality of colored light projection devices, each being adapted to generate a colored light in a corresponding projection zone. As explained above, each light projection device can for example include a group of three light projectors with primary colors Red, Green and Blue, the projectors being generally aimed at the same projection zone to superimpose their light outputs for additive color synthesis purposes. The light projectors may be polychromatic LEDs, incandescent projectors or the like. Each light projection device may however be embodied by other devices mentioned above or equivalents, as will be readily understood by one skilled in the art. The various light projection devices of a given light modulation system may be all of a same type, or alternatively different types can be used, in any desired combination.

The system further includes a plurality of light modulation devices each being operatively connected to a corresponding projecting device, for providing thereto modulated color component output signals for modulating the corresponding colored light.

Each light modulation device may correspond to any of the embodiments described above or equivalents thereof. Each light modulation device therefore includes a light modulator generating the color component output signals according to an intensity parameter and a color parameter. Either or both of the intensity and color parameter are controlled by a corresponding modulated signal. Each light modulation device also includes a modulation generator having a main Low Frequency Oscillator (LFO) generating an oscillating signal, and mixing means for mixing this oscillating signal of the main LFO with a base signal, thereby providing the modulated signal. Of course, each modulation generator may include is multiple LFOs as described above. The light modulation devices may also be adapted to provide independent intensity and color modulation of the corresponding colored light projected by the corresponding projecting device.

Each set composed of a given projection device and its associated light modulation device will be referred to below as a "Modulation Group".

A control unit for controlling each of the modulation devices is provided, so that the projection zones create together said dynamic patterns of light. The control unit may be embodied by a single stand-alone device, or by separate components in communication with each other. In another variant, the control unit may be joined with one or more of the modulation devices in a stand-alone control module device and linked in communication with the remaining components of the system. The control unit and/or light modulation devices may be integral to the light projection devices it provides the color component output signals to. It is further to be noted that the color component output signals from each light modulation device may be outputted separately or in a multiplexed fashion, using a variety of communication and control protocols, ranging from individual analog proportional intensity controls to multiplexed digital protocols such as the lighting industry standard DMX-512.

In some embodiments, the basic light modulation capabilities of the system can be greatly enhanced by using a number "N" of copies of such Modulation Groups, each copy driving it own set of three primary color light projectors to illuminate its own projection zone. As will be described below, entrancing visual effects can then be generated by the synchronized control of all modulation structures.

The "N" projections zones obtained from such a system can be organized in a variety of ways, depending on the geometry of the projection screen and the visual effects preferred. In one embodiment, the light projection devices are particularly arranged so that the projection zones are adjacent to each others; the control unit then controls each modulation devices in a predetermined manner so as to create controlled global movements of color and/or intensity in the patterns of light. This is best achieved by making use of the Phase Shift parameter "P" available for each modulation LFO, shown at 17 in FIG. 3, as will now be explained. Assuming "N" Modulation Groups driving "N" linearly adjacent projection zones have identical modulation structures, let us consider a LFO "LFOx" at a specific position in the structure. By assigning gradually increasing (or decreasing) Phase Shifts to LFOx in a succession of Modulation Groups, the waves produced by these LFOx will be sequentially delayed (or advanced) in the succession of Modulation Groups. Depending on the particular function of LFOx in the modulation structure, this will result in apparent movements of color or intensity in the matching projection Zones.

Figure 22A:
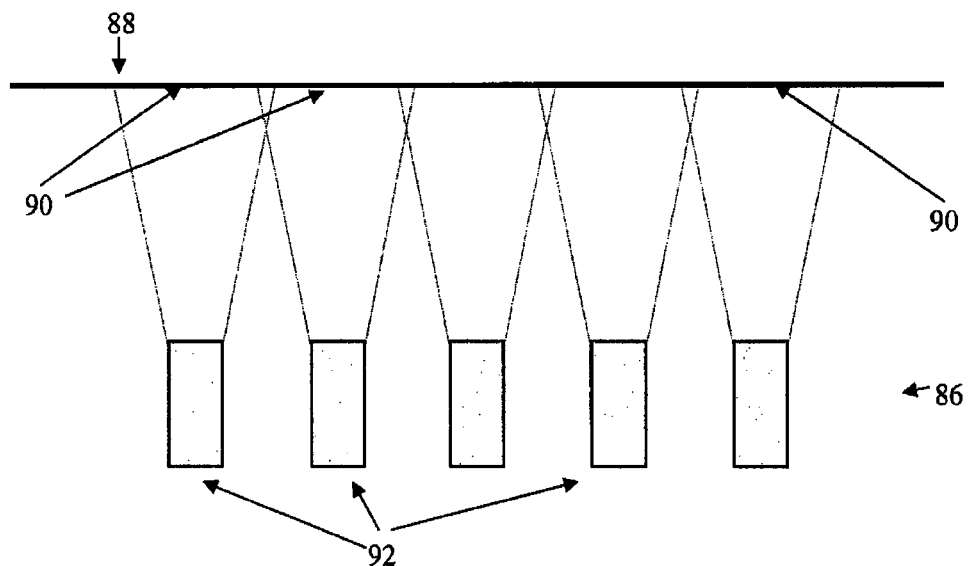
FIGS. 22A and 22B are respectively top and side views of a light modulation system using five projector groups that are linearly organized.
Figure 22B:
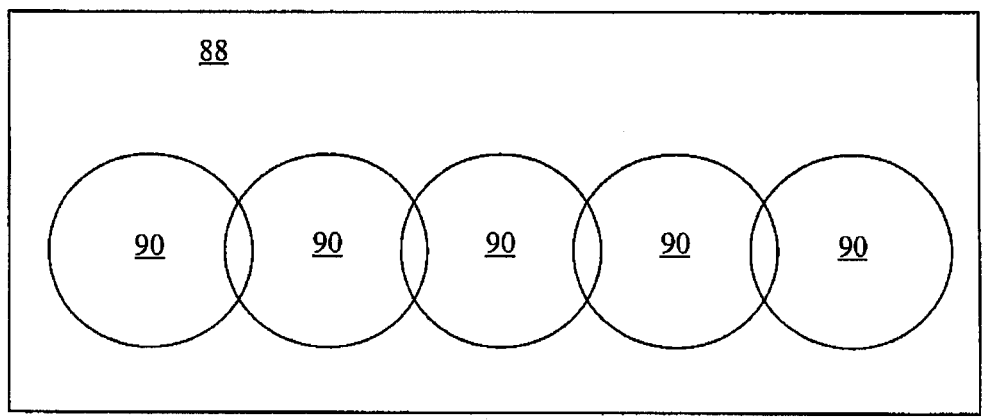

As an example, FIGS. 22A and 22B show the linear arrangement on a Projection Screen 88 of the Projection Zones 90 from the five Projector Groups 92 of a light modulation system 86 having five modulation Groups. The Projection Zones 90 may be overlapped, so as to create continuity in the visual effects on the Projection Screen 88. This arrangement generates a "light-wall" entirely adequate to create light modulation effects.

As will be shown in examples below, phase control of the LFOs in the modulation structure can generate visual effects moving across the projection zones array. A horizontal linear arrangement as shown in FIGS. 22A and 22B has the advantage of allowing visual effects exploiting the laterality of the eye/brain visual system, which clearly prioritizes left-right polarities in the visual field.

To illustrate how light movements can easily be generated with Phase Shift control of the LFOs, let us take an example where each Projection Zone shown in FIGS. 22A and 22B is driven by a Modulation Group having the modulation structure shown in FIG. 15 with one Intensity Modulation LFO "I1" and one Color Modulation LFO "C1", and with C1 parameters set to generate a color oscillation ranging between two colors Color1 and Color2. Let us name the Phase of LFO C1 in Modulation Group "n"="P.C1$_n$". Assuming a Phase range "P$_{range}$" of 360°, if we set P.C1$_1$=0°, P.C1$_2$=30°, P.C1$_3$=60°, P.C1$_4$=90° and P.C1$_5$=120°, the oscillation between Color1 and Color2 will be appear to shift from left to right on the Projection Screen 200. It has been observed that such light movement towards the right side of the perception field may have a tendency to enliven and stimulate the viewer, bringing him/her towards wakefulness. Inversely if for example we set P.C1$_1$=120°, P.C1$_2$=90°, P.C1$_3$=60°, P.C1$_4$=30° and P.C1$_5$=0°, the oscillation between Color1 and Color2 will be appear to shift from right to left on the Projection Screen 200. It has been observed that such light movement towards the left side of the perception field may have a tendency to calm and sedate the viewer, bringing him/her towards relaxation. Alternatively, if for example we set P.C1$_1$=0°, P.C1$_2$=60°, P.C1$_3$=120°, P.C1$_4$=60° and P.C1$_5$=0° the oscillation between Color1 and Color2 will be appear to shift from both left and right edges of the Projection Screen 200 towards its center, creating the illusion of an inward movement. It has been observed that such inward light movement towards the center of the perception field may have a tendency to create an introvert, centering atmosphere. Inversely, if for example we set P.C1$_1$=0°, P.C1$_2$=300°, P.C1$_3$=240°, P.C1$_4$=300° and P.C1$_5$=0° the oscillation between Color1 and Color2 will be appear to shift from the center of the Projection Screen 200 towards both left and right outer edges, creating the illusion of an outward movement. It has been observed that such light movement expanding towards the edges of the perception field may have a tendency to create an extrovert, stimulating atmosphere. Similar Phase Shifts applied to LFOs "I1" driving the light intensity of the Projection Zones will result in the apparent movement of shadows and bright regions across the Projection Screen, rather than movements of color as in the previous examples.

Figure 23:
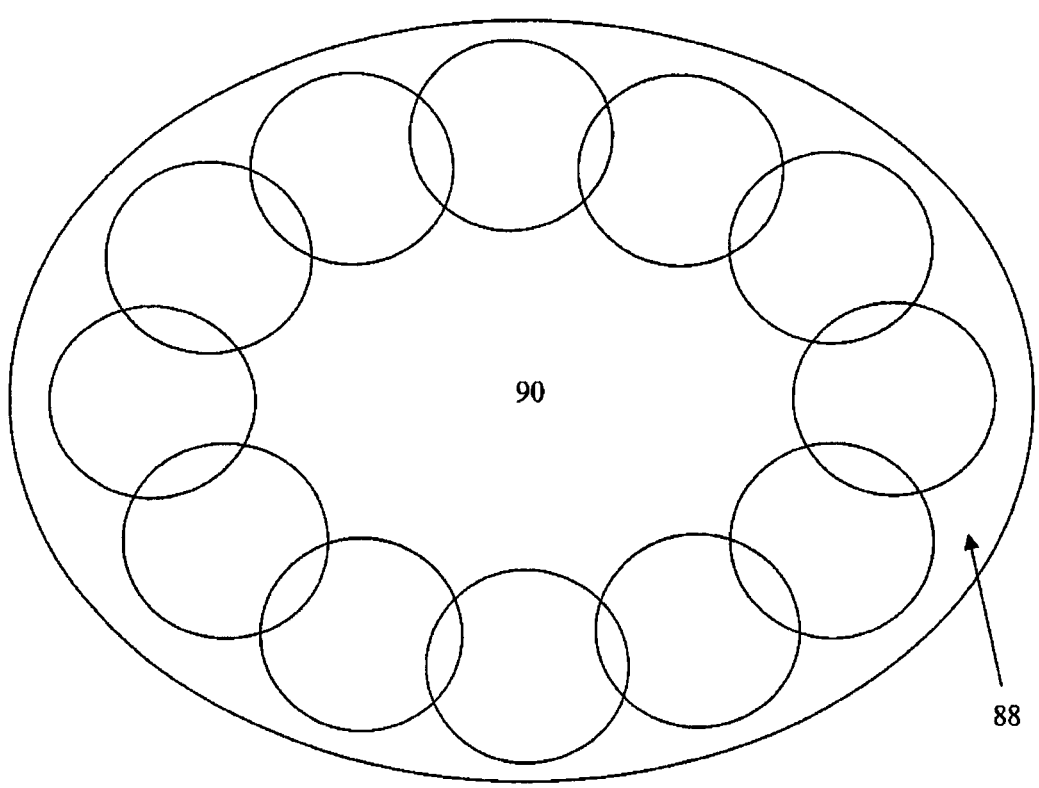
FIG. 23 shows the resulting light pattern from a light modulation system using twelve projector groups that are circularly arranged.

FIG. 23 shows another example of an arrangement for a system with twelve Modulation Groups, suitable for projection on a circular or elliptical Projection Screen 210. In this case, the twelve Projection Zones have a clockwise circular arrangement. For the purposes of modulation control, this arrangement is considered to be 1-dimensional.

Figure 24:
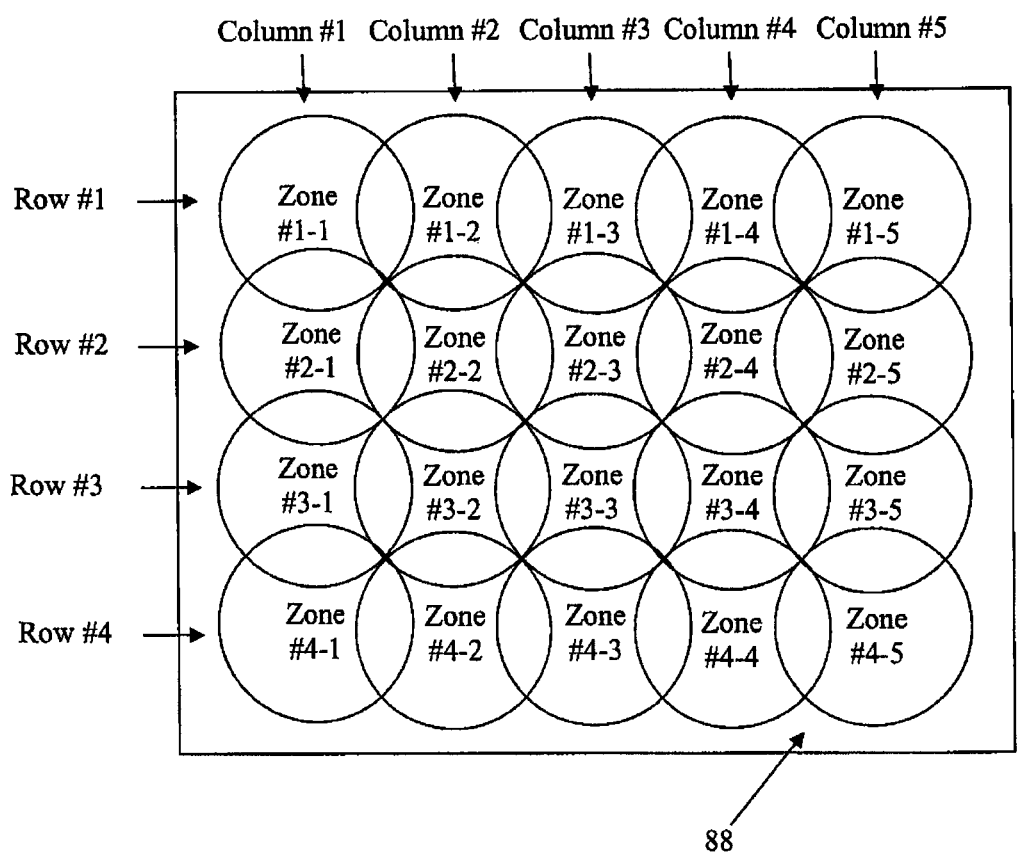
FIG. 24 shows the resulting light pattern from a light modulation system twenty projector groups that are arranged in rows and columns.

FIG. 24 shows an example of a 2-dimensional arrangement for a system with twenty Modulation Groups. Here the twenty Projection Zones are distributed in five Columns "C" by four Rows "R", and are designated as "Projection Zone #C-R".

This type of arrangement can be further extended to 3-dimensional installations which would include a number of Projection Screens or surfaces distributed along a third "Distance" axis.

Naturally, these examples do not limit in any way the possible arrangements of multiple Projection Zones for light modulation installations. Although interesting results will generally be obtained when the various Projection Zones overlap to form a continuous projection area, other interesting visual effects can be obtained with non-overlapping, arbitrarily distributed Projection Zones.

As previously shown in FIG. 3, each LEO in a light modulation system can have up to seven parameters "F", "D", "W", "R", "S", "P" and "M". Assuming each Modulation Group uses a modulation structure with a number "N$_{lfo}$" of LFOs, the total number of LEO parameters "P$_{lfo}$" to be controlled in each Nmg" Modulation Groups is equal to:

$$P_{lfo}=7*N_{lfo}$$ Equation 9

In addition, as previously shown in FIG. 11, the Light Modulator of each Modulation Group has two additional "P$_{mod}$" parameters: Base Intensity "I$_b$" and Base Color "C$_b$". The total number of parameters "P$_{mg}$" to be controlled in each Modulation Groups is therefore equal to:

$$\text{Equation}\ P_{mg}=P_{lfo}+P_{mod}=7*N_{lfo}+2$$ 10

For a light modulation system with "N" Modulation Groups, the total number "P$_{tot}$" of modulation parameters is therefore equal to:

$$P_{tot}=N*P_{mg}=N*(7*N_{lfo}+2)$$ Equation 11

In systems with many Modulation Groups each having a complex modulation structures, the total number of parameters "P$_{tot}$" can become quite large. For example with a system of twenty Modulation Groups each having twelve LFOs, we obtain: P$_{tot}$=20*(7*12+2)=1720 parameters.

Such a large number of independent parameters may in some circumstance be impractical to control. In some embodiment, interesting visual effects can be obtained with synchronized projection zones, which may be achieved by organizing the modulation parameters in ways simplifying and unifying the control of the whole structure. According to one embodiment of the invention, this may be achieved by introducing for each of the "P$_{mg}$" modulation parameters a new parameter designated as "Global", which allows the simultaneous control of its matching individual parameters in all "N" Modulation Groups. Various methods of combining the Global parameter with the individual parameters of each Group are possible. We will describe hereinbelow some illustrative methods which lead to visually effective results. It is to be understood that these examples are not limitative of other combination methods obeying to the principle of allowing global control of a parameter for all Modulation Groups with a single Global value, while retaining the functionality of individually offsetting values of specific Modulation Groups.

For example, let us consider any modulation parameter "X" in a light modulation system with "N" identical Modulation Groups. Each Modulation Group "n" has its own instantiation of the parameter "X" which we will designated "X$_n$"; we will therefore have N individual Parameters X$_1$, X$_2$, ..., X$_N$. We will now define a new "Global X" parameter designated "X$_G$" which will be used to globally scale all of the individual "X$_n$" parameters. The specific scaling method will depend on the parameter type: we can classify the various modulation parameters into the four types shown in Table 2, each with its own global method.

TABLE 2

| Parameter Type: | Multiplicative | Additive | Modulo | Discrete |
|---|---|---|---|---|
| LFO Parameters: | | | | |
| Frequency "F" | | | X | |
| Depth "D" | X | | | |
| Waveshape "W" | | | | X |
| Duty Cycle "R" | X | | | |
| Symmetry "S" | X | | | |
| Phase Shift "P" | | | X | |
| Oscillation Mode "M" | | | | X |
| Light Modulator Parameters: | | | | |
| Intensity "I" | X | | | |
| Color "C" | | | | X |

Global Scaling may be realised in the following way for parameters of the "Multiplicative" type:

$$X\ \text{for Modulation Group}\ \#n=X_G*X_n/X_{range}$$ Equation 12 by way of example, let us look at a typical modulation structure composed of five Modulation Groups as shown in FIGS. 22A and 22B, each composed the 3-LFO structure shown in FIG. 18. Taking for example the Depth parameter of Intensity Modulation LFO #I1 designated "I1D", we will have five individual control values (one for each of the Modulation Group) designated as "I1D$_n$", and a Global value designated "I1D$_G$". The effective value used to control the LFOs will be given by:

$$I1D \text{ for Group } \#n = I1D_G * I1D_n / I_{range} \qquad \text{Equation 13}$$

Assuming for example I1D$_G$=80 and I1D$_3$=50, since I$_{range}$=100 we have I1D(Group 3)=80*50/100=40.

Global Scaling may be effected in the following way for parameters of the "Additive" type:

$$X \text{ for Modulation Group } \#n = X_G + X_n \qquad \text{Equation 14}$$

Taking for example the Frequency parameter of Intensity Modulation LFO #I1 designated as "I1F", we will have five individual values (one for each of the Modulation Group) designated as "I1F$_n$", and a Global value designated "I1F$_G$". The effective value used to control the LFOs will be given by:

$$I1F \text{ for Group } \#n = I1F_G + I1F_n \qquad \text{Equation 15}$$

Assuming for example I1FG=20 and I1F3=100, we have I1F(Group #3)=20+100=120.

Since as described previously the Frequency parameter is logarithmic, the addition of the parameters actually corresponds to a multiplication of the frequency values; in this example, the individual frequency set to 1 Hz (I1F$_3$=100) is multiplied by two (I1F$_G$=20) resulting in an effective frequency of 2 Hz for LFO I1 in Group #3. It is to be noted that if an alternative method of using a linear Frequency parameter was selected, it may be preferable to apply the Multiplicative method of combining global and individual Frequency values, since human perception of pulsations is more attuned to a logarithmic scale.

Global Scaling may be effected in the following way for parameters of the "Modulo" type:

$$X \text{ for Modulation Group } \#n = (X_G + X_n) \text{modulo } X_{range} \qquad \text{Equation 16}$$

Taking for example the Base Color parameter of Light Modulator designated as "Cb", we will have five individual values (one for each of the Modulation Group) designated as "Cb$_n$", and a Global value designated "Cb$_G$". The effective value used to control the Light Modulators will be given by:

$$Cb \text{ for Group } \#n = (Cb_G + Cb_n) \text{modulo } C_{range} \qquad \text{Equation 17}$$

Assuming for example Cb$_G$=108 and Cb$_3$=50 (green color), since G$_{range}$=128 we have Cb(Group #3)=(108+50) modulo 128=30, i.e. yellow.

Global Scaling may be effected in the following way for parameters of the "Discrete" type:

if X$_n$ is equal to default X value:

$$X \text{ for Modulation Group } \#n = X_G$$

else:

$$X \text{ for Modulation Group } \#n = X_n \qquad \text{Equation 18}$$

The resultant functionality is to have the Global parameter override the Individual parameter only if it is set to its default value, otherwise keep the Individual parameter as is. For example assuming the default value for Waveshape parameter "W" is specified as being 1 (e.g. sinewave), looking at the Waveshape parameter of Intensity Modulation LFO #I1 designated as "I1W", we will have five individual values (one for each of the Modulation Group) designated as "I1W$_n$", and a Global value designated "I1W$_G$". If I1W$_3$=1, the effective value used to control LFO I1 Waveshape in Group #3 will be the Global value I1W$_G$; if I1W$_3$=2 this value will determine the LFO Waveshape and the Global value I1W$_G$ will be ignored. This Global scaling method facilitates globally setting discrete parameters with a single Global parameter, while preserving special individual settings for some of the Groups.

In the case of 2-D projection zones arrangements organized in an array having H rows and V columns, in addition to Global parameters "X$_G$" it is desirable to further define a number H of "Row" parameters "XR$_h$" and a number V of "Column" parameters "XC$_v$" to facilitate the separate control of global horizontal and vertical visual effects. In this case the individual parameters "X" will be scaled by the triple combination of "X$_G$", "XR$_h$" and "XC$_v$", with the scaling method depending on the type of the parameter as defined in Table 2.

Again by way of example, let us look at a 2-D modulation structure composed of twenty Modulation Groups as shown in FIG. 24, where H=4 and V=5, each composed the 3-LFO structure shown in FIG. 18. Let us assume the Modulation Group #3 is assigned to Projection Zone #1-3, with H=1 and V=3. Taking for example the case of the Phase parameter (defined as being of the Modulo type) for LFO #I1 for Group #3 with an individual parameter designated as "I1P3", we will have:

$$I1P(\text{Group \#3}) = (I1P_G + I1P_{R1} + I1P_{C3} + I1P_3) \text{modulo } 360° \qquad \text{Equation 19}$$

where I1P$_G$ is the Global value for the LFO #I1 Phase parameter, I1P$_{R1}$ is its value for Row #1 and I1P$_{C3}$ is its value for Column #3.

Fabrication Method

In accordance with another aspect of the invention, there is provided a method for manufacturing a light modulation system for creating non-representational dynamic patterns of light. The method includes the assembly of electronic components capable of performing the function of:

providing a plurality of colored light projection devices, each being adapted to generate a colored light in a corresponding projection zone;

providing a plurality of light modulation devices and operatively connected each said light modulation device to a corresponding projecting device for providing thereto modulated color component output signals for modulating the corresponding colored light, each light modulation device comprising:

a light modulator generating said color component output signals according to an intensity parameter and a color parameter, at least one of said intensity and color parameter being controlled by a corresponding modulated signal; and a modulation generator for generating the corresponding modulated signal, the modulation generator being in communication with the light modulator for providing the modulated signal thereto, said modulation generator having a main Low Frequency Oscillator (LFO) generating an oscillating signal and mixing means for mixing said oscillating signal of the main LFO with a base signal, thereby providing said modulated signal; and providing a control unit for controlling each of said modulation devices so that the projection zones create together said dynamic patterns of light.

It is to be understood that any appropriate method of assembling, building, programming, connecting the components above may be used without departing from the scope of the present invention.

Applications

Generally speaking, embodiments of the present invention provide a method for generating non-representational dynamic patterns of light. This method includes:

a) providing a plurality of colored light projection devices, each being adapted to generate a colored light in a corresponding projection zone;
b) providing modulated color component output signals to each of said light projection devices, comprising:
   i) generating said color component output signals according to an intensity parameter and a color parameter, at least one of said intensity and color parameter being controlled by a corresponding modulated signal; and
   ii) for each of said corresponding modulated signal, generating an oscillating signal using a main Low Frequency Oscillator (LFO), and mixing said oscillating signal of the main LFO with a base signal, thereby providing the modulated signal; and
c) controlling each of said modulation devices so that the projection zones create together said dynamic patterns of light.

As mentioned above, the light modulation devices and systems of the present invention can be used in a variety of contexts. Non-exhaustive examples of applications of the present invention are given below.

While it is to be understood that light modulation projections have a subtle, non-invasive effect, their relaxing or uplifting properties are nevertheless capable of exerting a beneficial influence in reducing stress level of users and therefore assist in the treatment of numerous stress-related pathologies. Visual effects generated by light modulation are for example effective in immersive projection environments, where their psychoactive properties can best be used for applications with potentially therapeutic purposes in fields where relaxation and sensory stimulation are known to be beneficial. Examples of potential therapeutic areas of applications include: treatment of sleep disorders, treatment of addictions, rehabilitation of cerebral poly-traumatisms, pre-surgery preparation and relaxation, experimental cancer healing modalities involving positive visualization, behavioural therapy and peak-performance sports training.

Since Light Modulation projections are especially conducive to relaxation and mood lighting, a possible usage of the invention consists in attaching a Light Modulation projection device and matching projection screen to a well-being chair, table or bed in such a way as to present the light projection to the user's field of view as he/she reclines on the relaxation surface.

Figure 25:
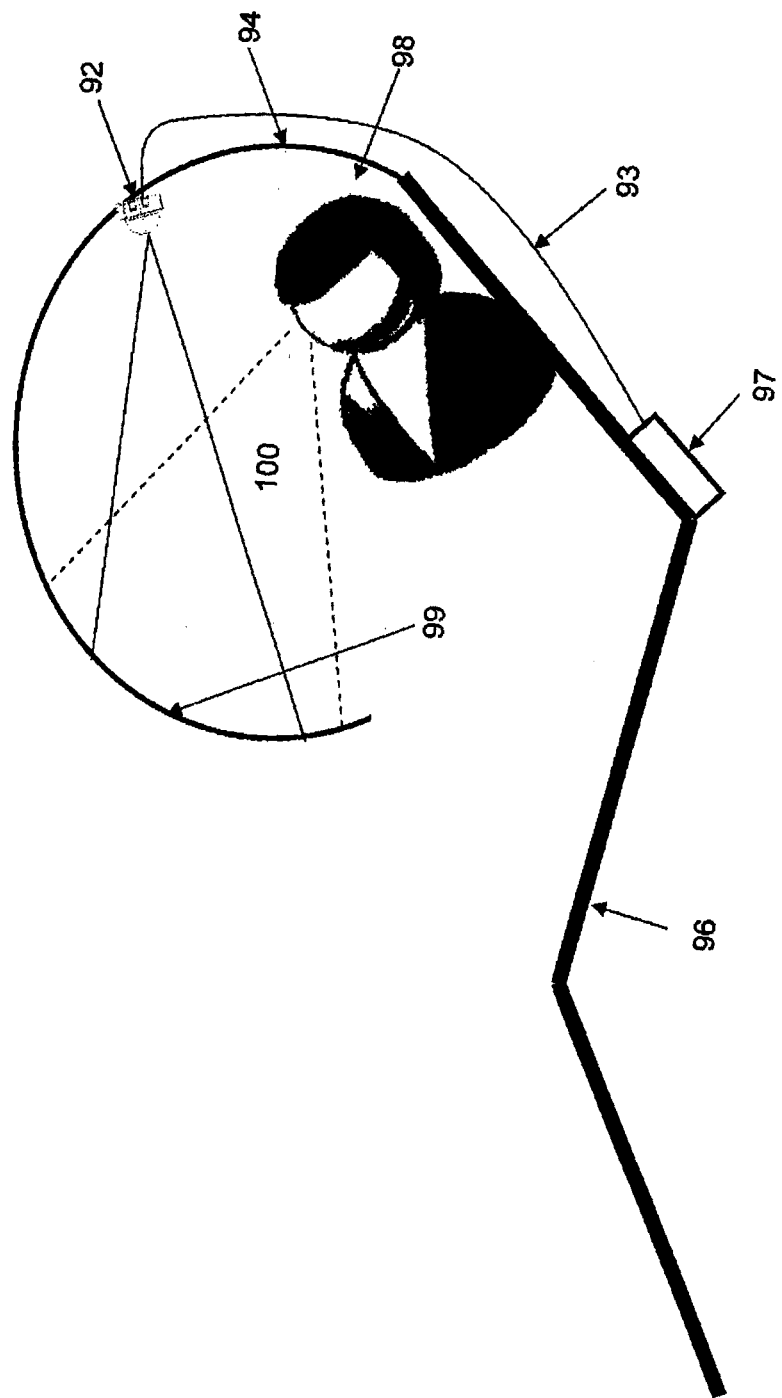
FIG. 25 shows a well-being chair equipped with a light modulation system according to an embodiment of the invention.
Figure 29A:
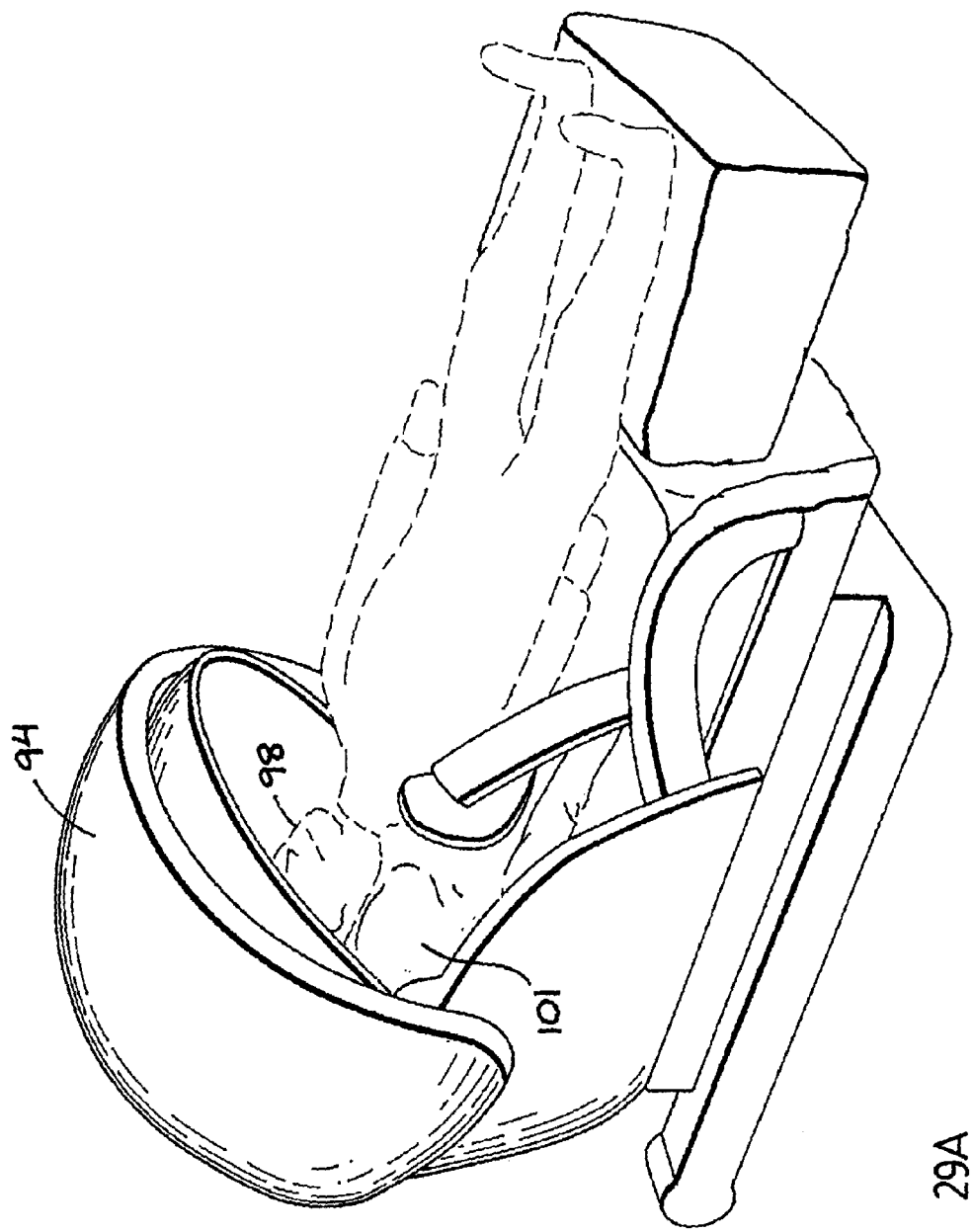
FIG. 29A is a perspective view of a well-being chair according to an embodiment of the invention.

With reference to FIGS. 25, 29A and 29B, according to a particular embodiment of the invention, there is therefore provided a system including a well-being chair 96 for receiving a user and having a head portion 101 for receiving the head 98 of this user. The system further includes a projection shell 94 mounted over the head portion 101 of the well-being chair 96, and a light modulation system according to any of the embodiments above or equivalents thereto mounted proximate the head portion. The light modulation system is positioned to project the non-representational dynamic patterns of light inside the projection shell.

In the examples illustrated in FIGS. 25, 29A and 29B, the systems include a light projection group 92, controlled though a communication link 93 by a light modulation control module 97. On skilled in the art will understand that alternatively, a plurality of projection groups may be provided at different locations within the projection shell. Also alternatively, the control module may be integrated to the projection group or to individual projecting devices. The projection shell 94 (or "cocoon") is attached to the well-being chair 96 and surrounding the user's head 98. The light projection group 92 is oriented and focused in such a way as to illuminate a light projection area 99 in the user's field of view 100.

The projection shell 94 may be mechanically activated to be lowered over the user's head 98 while he/she is reclining on the chair 96, and subsequently brought up out of his/her way to facilitate sitting on the chair and moving out of it. An example of a suitable well-being chair 96 with mechanically movable head shell is the uSpace model OS-7000 made by OSIM International Ltd (Singapore).

Figure 26:
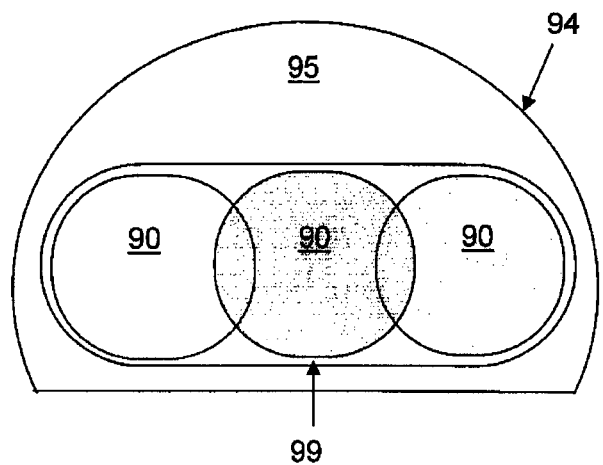
FIG. 26 schematically illustrates the field of view of a user in a chair as shown in FIG. 25.

FIG. 26 shows the light projection area 99, viewed from the user's point of view as he/she reclines on the relaxation chair. In this example, three Modulation Groups each generate a color zone 90 projected on the inner surface 95 of the chair's head shell 94. Such color zones can be obtained with a light projection device 335 using, for example, one RGB LED per Modulation Group. An example of suitable RGB LED is the P1 Z-Power model F10392 from Seoul Semiconductor Ltd (South Korea) with integrated 1W Red, Green and Blue dies, coupled with a focusing lens such as the PL19825 from Kathod (Italy) having a 25° output beam. The color zones overlap in order to illuminate a continuous projection area 350 and thus enable complex Light Modulation projections with embedded pulsations for the exclusive and private benefit of the user reclining on the well-being chair.

Optionally, the well-being chair can contain an automated massage mechanism, and the massage and light projections can be harmonized in order to create an enhanced wellness experience for the user. For example, to accompany a soft relaxing massage sequence the light projector can generate light modulation patterns with slow rhythms (typically longer than 1 second) that tend to soothe and relax. Alternatively, to accompany an energetic massage sequence the light projector can generate light modulation patterns with fast rhythms (typically shorter than 1 second) that tend to stimulate and waken up.

Light Modulation patterns can also be projected on a larger scale in order to generate environmental light effects for a whole room. Such projections can be made directly on reflective walls of the room, or alternatively on one or more projection screens for better visual results. The projection surface may be flat, or preferably it may be curved around the viewer so as to provide a more immersive visual impression.

Figure 27:
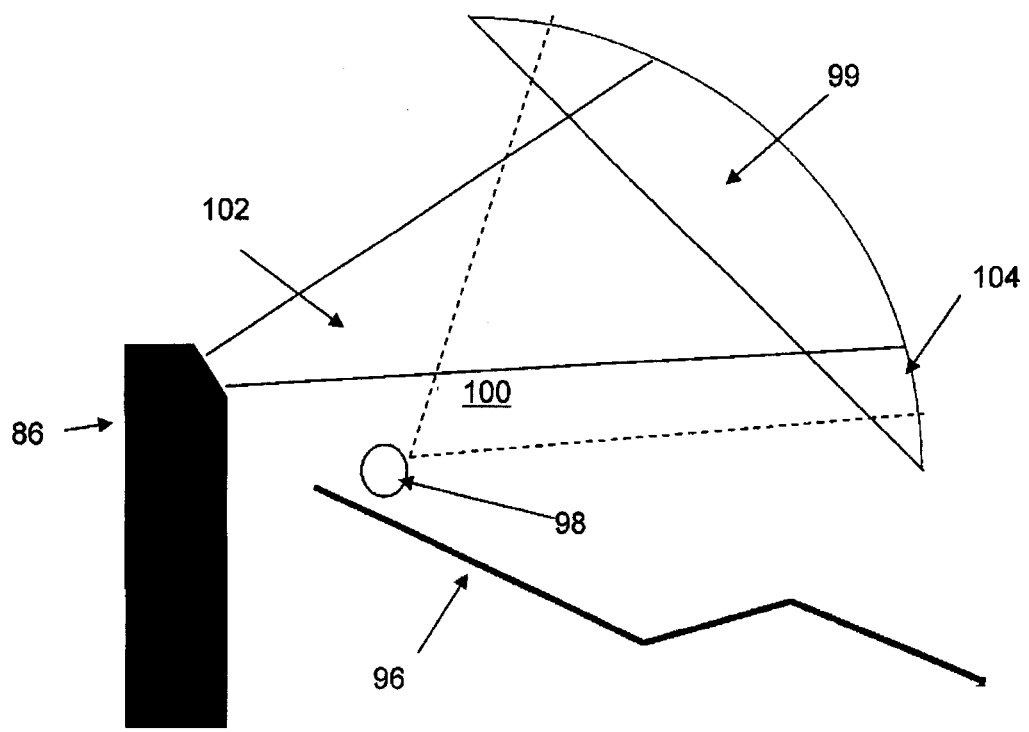
FIG. 27 shows a relaxation room equipped with a light modulation system according to an embodiment of the invention.

An example of such an immersive system is the Sensora made by Sensortech Inc. (Canada), schematically shown in FIG. 27. In this system, a light projection system 86 containing multiple Modulation Groups generates an output light beam 102 projected towards a large hemispherical projection screen 362 having a diameter of 3.3 m. The screen is attached to the room walls and is oriented at 45° inclination towards the user 98 lying on a reclining relaxation chair 96 at a distance of about 2.5 m, such that the projected surface covers most of the user's field of view 100. This creates a multi-zone light projection area similar to that shown in FIG. 26, but on the scale of the whole room. An advantage of projection at room-scale is to create a more welcoming, open and non-claustrophobic relaxation environment when compared with smaller light projection systems attached to a chair or integrated in goggles. The room itself is preferably light-proof and sound-proof, so as to provide a deeply relaxing environment where the Light Modulation patterns can optionally be combined with other sensorial stimulation such as sound, kinesthetic vibrations in the relaxation chair and aromatic smells. Such a room can for example be used as a private relaxation room in a spa or resort, or as a room for individual psychotherapy sessions assisted by light therapy.

Light modulation projections on the scale of a room can be used in various other ways. An example is a room with many chairs under a wide projection surface, which can be used as a waiting room in airports, offices, . . . or a public relaxation room at a spa or resort. Another example is to transform a private bedroom into an exquisite and soothing light environment by projecting Light Modulation patterns on the ceiling of the room. Yet another example is to illuminate with Light Modulation patterns a whole wall of a hotel or office building lobby, a restaurant or a bar, to create an impressive light environment. Yet another example is creating a dome-shaped room, or a room with a party curved shape, and use the curved walls directly as projection screens for Light Modulation patterns, resulting in remarkable immersive light environments.

Light Modulation patterns is also ideally suited to complement existing stage lighting techniques for public performances, because they enable for the first time a new class of spectacular lighting effects based on the safe use of light pulsations, with minimal risk of detrimental effects on photosensitive people compared to traditional stroboscopic effects.

Many types of standard tri-color stage lighting projectors already integrate the three primary colors (Red, Green and Blue) enabling Light Modulation effects (for example: LED-based luminaire model P64 from American DJ Supply). Alternatively a set of standard single-color light projectors of arbitrary power with Red, Green and Blue filters can be aimed on the same spot to create a Modulation Group projection area. An arbitrary number of such Modulation Groups can be controlled by a Light Modulation processor, typically through an industry-standard protocol such as DMX-512.

A typical application is to use a linear array of Modulation Groups illuminating the whole width of a backdrop screen for a stage production, such as in theatre, dance or music concert venues, as shown in FIG. 23.

Alternatively the projection zones of each Modulation Group can be arranged in various one-, two- or three-dimensional arrays (as exemplified in FIGS. 23 and 24) to create innovative light projection installations capable of displaying complex Light Modulation effects.

In another application, color lighting systems are already used more and more frequently to illuminate architectural landmarks. They typically are used to perform gradual, uniform color changes over the projection surface to create an attractive lighting atmosphere. Such lighting atmospheres can be greatly enhanced by using Light Modulation to control the lighting system.

Light Modulation can be used to illuminate large-scale architectural structures, such as buildings, billboards or bridges by using arrays of commercially available RGB light projectors. The structure's surface is divided into an arbitrary number of projection zones, each one being illuminated by one Modulation Group. The projection zones will preferably be adjacent and overlapping so as to create continuous light effects spreading over the whole structure when applying synchronized Light Modulation effects, Referring to FIG. 28, according to another embodiment of the invention, a system including a headwear implement for wearing on a head of a user is provided. The headwear implement may for example be embodied by goggles, a helmet, or any other structure which may be worn on one's head. The headwear implement includes a projection shell extending in a field of view of the user. A light modulation system according to any of the embodiments above or equivalents thereto is mounted on the headwear implement and positioned to project the non-representational dynamic patterns of light inside the projection shell.

Wearable goggles and eyesets illuminated with pulsing LEDs or other internal light sources have long been available for the purpose of photic brainwave entrainment, such as for example the TruVu Omniscreen eyesets from Mind Alive Inc. (Canada). Because they commonly contain light sources with a single color, these eyesets are usually not compatible with Light Modulation which works best with multi-color (such as RGB) light sources for color modulation.

FIG. 28 shows one example of light goggles 106 optimized for Light Modulation and adapted to be worn in front of the eyes 114 of a user. In this example, each half 108 of the goggles 106 is equipped with five light projection devices 110 embodied by RGB LED light sources laterally spread over the goggle's width, each illuminating its own projection zone 90 on a projection substrate 112 made with diffusing translucent material. The LED positions and output beam width are chosen so that their resultant projections zones overlap across the projection surface, resulting on a continuous light projection area spread laterally over the user's field of view 100. Each RGB LED can act as an independent Modulation Group when controlled by a Light Modulation control module 97 through a communications link 93. In another embodiment of a wearable light modulation device, a light projection assembly similar to 108 can be used to illuminate the visor of a helmet-type head shell, thereby generating a continuous light projection area spread laterally over the user's field of view 100.

Such Light Modulation goggles can generate complex fluid light patterns with embedded pulsations. While these light patterns are naturally suitable for photic brainwave entrainment, they also enable more sophisticated light processes. The use of multi-color light patterns introduces an aesthetic component which can significantly enhance the attractiveness of the light projection, and potentially enhance its therapeutic value. Synchronized phase control of the multiples Modulation Groups allow the generation of light patterns with laterally moving intensity and/or color waves which can be used to influence the visual system's laterality properties. The capability to independently control the left and right portions of the field of view of both eyes enables a precise control of the visual influence over the left and right parts of the brain's visual cortex in spite of the well-known crossing-over of the optic nerve fibres in the optic chiasma.

Methods allowing relaxation, stimulation or mood stabilization in humans or animals, making use of at least one embodiment of the invention, constitute in themselves an object of the invention.

Therapeutic methods for treatment of nervous system dysfunctions and of any human or animal pathology brought about by excessive stress levels, making use of at least one embodiment of the invention, likewise constitute in themselves an object of the invention.

Careful setting of the various control parameters of a light modulation system, with appropriate sequencing of such parameter sets to create light modulation sessions, combined with exposure to such light modulation sessions at selective rate (e.g. once per day, once per week, or according to the user's request) and overall treatment duration, allow the generation of specific mood-enhancing or therapeutic effects beneficial to humans or animals viewing the light projections created by the invention.

The light modulation system allows full control of the colors and brainwaves photic driving properties of a light projection. Furthermore they allow the control of cyclic light movements: as previously described, through coordinated phase control of the intensity and/or color parameters it is possible to generate apparent movement patterns in the light projection. Patterns such as a left-to-right linear movement, a clockwise circular movement or an outward movement expanding from the center of the visual field towards the edges have a subtle tendency to bring arousal and stimulation.

Conversely patterns such as a right-to-left linear movement, a counter-clockwise circular movement or an inward movement contracting from the edges towards the center of the visual field have a subtle tendency to bring pacification and introversion.

The proper combination of all these elements brings light projections with enhanced effects. For example, light projections with enhanced relaxing and pacifying effects are obtained by using various combinations of colors in the cool-color range with brainwave modulations in the Alpha-range and left-oriented, inward or counter-clockwise light movements. Light projections with enhanced energizing and stimulating effects are obtained by using various combinations of colors in the warm-color range with brainwave modulations in the Beta-range and right-oriented, outward or clockwise light movements. Light projections with enhanced balancing and mood-stabilizing effects can be obtained by using intermediate colors, or alternatively colors uniformly cycling across the whole rainbow spectrum, which can easily be obtained by for example setting the Depth parameter "D" of color modulation LFO $40c$ equal to the full range color range $C_{range}$. Examples of light movements compatible with said balancing light effects include sequences respectively presenting in equal proportions both left-oriented and right-oriented, or inward and outward, or clockwise and counter-clockwise patterns; another example is the use of randomized light movements, easily obtained by setting the frequency parameter of intensity or color modulation LFOs to nearly equal but slightly different values for each Modulation Group, leading to random-looking beat effects between projection zones. Examples of brainwave modulations compatible with said balancing light effects include using the particularly harmonious Schumann Resonance frequency (7.8 Hz), or continuously sweeping back and forth through a range of frequencies from Beta to Theta.

Moderate variations in the control parameters allow the creation of light projections which vary enough to prevent boredom and captivate the user's attention while retaining a specific psychophysiological effect. Sequences of light projections with such moderate variations can be assembled to create complete light sessions.

Light projections sessions combining predetermined sequences of light projections with relaxing, stimulating and balancing effects can also be created. For example, it may be beneficial to conclude a 20 minutes session using relaxing light projections with 2 minutes of stimulating light projections in order to help the user to emerge with refreshed energy from the session. It is also possible to create light patterns simultaneously combining elements of different types within the same light projection to create a variety of hybrid effects, for example by combining a relaxing cool color such as turquoise with stimulating light movements in the outward direction.

Sessions optimized for casual, recreational mood-enhancing use (for example in spas and resorts) can be created by restricting the modulation depth parameters to low values (typically 5% to 10%), and by continuously varying the light projections in subtle ways, thereby limiting the psychophysiological impact to a level safe for all users. Session durations of 10 to 30 minutes have been found to be effective for this application, with 20 minutes being the optimal compromise between effectiveness and best time usage of the system.

Sessions optimized for more intense use in a therapeutic context can be created by allowing a deeper range of modulation depth (for example up to 20-50%), thereby increasing the psychophysiological impact. Such sessions can be more precisely targeted, for example by maintaining a specific light movement, color and brainwave frequency combination for a significant period of time (i.e. more than 1 minute). Such sessions are preferably performed under the supervision of a therapist capable of monitoring the effects of the light projections through appropriate means, including for example psychological testing, and/or monitoring of physical functions such as electroencephalograpic waves (EEG), electrocardiogram (ECG), skin resistance (ESR), or heart-rate variability (HRV). Such monitoring allows the selection of light modulation parameters adapted to the user's needs as they evolve. A complete therapeutic process assisted by light modulation can consist of a sequence of such sessions given over a period of time sufficient to have a lasting therapeutic effect. For example, a complete therapy course could consist of a weekly regimen of two sessions of 30 minutes each lasting for 6 weeks.

A further object of the invention is constituted by the methods of influencing the nervous system of a user for recreational purposes by exposing the user to light projections generated by a light modulation system according to the present invention and using predetermined combinations of control parameters selected to generate visual effects leading to at least one of the following effects: relaxation, stimulation, mood stabilization or balancing.

Those methods of the invention of influencing the nervous system of a user for recreational purposes, wherein a relaxing effect is obtained by exposing the user during 5-60 minutes to light modulation projections with colors in majority within the cool-color range comprised between green and blue, combined with light movements oriented in majority towards the left, inward or counter-clockwise directions and brainwave intensity modulation in majority within the Alpha and Theta frequency range of 4 to 13 Hz, are of a particular interest.

Also those methods of the invention of influencing the nervous system of a user for recreational purposes, wherein a stimulating effect is obtained by exposing the user during 5-60 minutes to light modulation projections with colors in majority within the warm-color range comprised between red and yellow, combined with light movements oriented in majority towards the right, outward or clockwise directions, and combined with brainwave intensity modulation in majority within the Gamma and Beta frequency range of 14 to 100 Hz, are of a particular interest.

Furthermore, those methods of the invention influencing the nervous system of a user for recreational purposes, wherein a mood-stabilizing or balancing effect is obtained by exposing the user during 5-60 minutes to light modulation projections with colors either going through the full rainbow spectrum or in majority composed of intermediate colors lime or magenta, combined with alternations in substantially equal proportions of light movements having complementary relaxing or stimulating properties, are particularly interesting.

Particularly interesting are those methods of influencing the nervous system of a user for recreational purposes wherein:

a relaxing effect is obtained by exposing the user during approximately 20 minutes to light modulation projections with colors comprised between green and blue, combined with light movements oriented towards the inward direction and low-depth (5-10%) brainwave intensity modulation in the Alpha frequency range of 8 to 13 Hz.

a stimulating effect is obtained by exposing the user during approximately 20 minutes to light modulation projections with colors comprised between red and yellow, combined with light movements oriented the right direction and low-depth (5-10%) brainwave intensity modulation in the Beta frequency range of 14 to 30 Hz; and a mood-stabilizing or balancing effect is obtained by exposing the user during approximately 20 minutes to light modulation projections with colors going through the full rainbow, combined with alternations in substantially equal proportions of light movements having inward and outward directions and low-depth (5-10%) brainwave intensity modulation near the frequency of 7.8 Hz.

An additional object of the present invention is a therapeutic method of treating the nervous system of a patient by exposing the patient to light projections generated by a light modulation system of the invention using predetermined combinations of control parameters selected to generate stress-reducing visual effects leading to at least one of the following effects: relaxation, stimulation, mood stabilization or balancing.

Preferably, those therapeutic methods of treating the nervous system of a patient comprise at least one step wherein the patient is exposed to at least one of the methods of influencing the nervous system according to the invention.

Those therapeutic methods comprising additional steps using at least one of the following treatment types: therapy based on the effects of drugs, therapy based on bodywork such as massage, therapy based on vibrational effects, or psychological counseling, are of a particular interest.

Additionally, those therapeutic methods comprising the following specific steps: exposing the patient to a series of 3 to 15 light projection sessions within a treatment period of 1 to 12 weeks, are very efficient for the intended purpose.

It is to be understood that the invention is not limited in its application to the details is of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of illustrative embodiments thereof, it can be modified, without departing from the spirit, scope and nature of the subject invention.

The invention claimed is:

1. A light modulation device for generating modulated color component output signals adapted for use by a light projection device for modulating light projected thereby, the light modulation device comprising:
an electronic circuit, comprising:
a light modulator generating said color component output signals according to an intensity parameter for controlling a brightness of said light and a color parameter for controlling a hue of said light, the color parameter being controlled by a modulated color signal; and
a color modulation generator for generating the modulated color signal, the color modulation generator being in communication with the light modulator for providing the modulated color signal thereto, said color modulation generator having:
a main Low Frequency Oscillator (LFO) generating an oscillating signal; and
a color mixer performing a summation of said oscillating signal of the main LFO with a base color signal, thereby providing said modulated color signal, said color mixer comprising a modulo summation element such that:

$$C_{combined}(t) = (C_b(t) + C_{lfo}(t)) \bmod C_{range};$$

wherein t represents time, $C_{combined}(t)$ is the modulated color signal, $C_b(t)$ is the base color signal, $C_{lfo}(t)$ is the oscillating signal and $C_{range}$ is a maximum authorized value for $C_b(t)$ and $C_{lfo}(t)$.

2. The light modulation device according to claim 1, wherein the intensity parameter is controlled by a modulated intensity signal, said light modulation device further comprising an intensity modulation generator for generating the modulated intensity signal, the intensity modulation generator being in communication with the light modulator for providing the modulated intensity signal thereto, said intensity modulation generator having:
a main Low Frequency Oscillator (LFO) generating an oscillating signal; and
an intensity mixer multiplying_said oscillating signal of the main LFO with a base intensity signal, thereby providing said modulated intensity signal.

3. The light modulation device according to claim 1, wherein said color modulation generator further comprises at least one additional LFO generating an additional oscillating signal, the color mixer performing a summation of said additional oscillating signal with said oscillating signal, thereby allowing a complex modulation of said light projected by said light projection device.

4. The light modulation device according to claim 3, wherein the oscillating signal and additional oscillating signal have distinct predetermined frequencies selected so that said complex modulation combines simultaneous slow and fast modulations.

5. The light modulation device according to claim 3, wherein said color modulation generator comprises:
a first modulation set including said main LFO and at least one control LFO operatively connected to the main LFO for controlling at least one of waveform parameters of the oscillating signal; and
a second modulation set including said additional LFO and at least one control LFO operatively connected to the additional LFO for controlling at least one of waveform parameters of the additional oscillating signal.

6. The light modulation device according to claim 1, wherein said color modulation generator comprises at least one control LFO operatively connected to the main LFO for controlling at least one of waveform parameters of the oscillating signal for allowing a complex modulation of said light projected by said light projection device.

7. A light modulation device for generating modulated color component output signals adapted for use by a light projecting system for modulating light projected thereby, the light modulation device comprising:
an electronic circuit, comprising:
a light modulator generating said color component output signals according to an intensity parameter for controlling a brightness of said light and a color parameter for controlling a hue of said light, said color parameter being controlled by a color complex modulated signal; and
a complex color modulation generator generating said color complex modulated signal, the complex color modulation generator being in communication with the light modulator for providing the color complex modulated signal thereto, said complex color modulation generator having a plurality of Low Frequency Oscillators (LFO) each generating an oscillating signal, the color complex modulated signal resulting from a combination of the oscillating signals of each of said LFOs, said complex color modulation generator comprising a color mixer performing a summation of the oscillating signal of at least one of said LFOs with a base color signal, thereby providing a combined color signal, said color mixer comprising a modulo summation element such that:

$$C_{combined}(t)=(C_b(t)+C_{lfo}(t)) \text{modulo } C_{range};$$

wherein t represents time, $C_{combined}(t)$ is the combined color signal, $C_b(t)$ is the base color signal, $C_{lfo}(t)$ is the oscillating signal of the corresponding LFO and $C_{range}$ is a maximum authorized value for $C_b(t)$ and $C_{lfo}(t)$.

8. The light modulation device according to claim 7, wherein said color mixer performs a summation of the oscillating signals from at least two of said LFOs, said oscillating signals having distinct predetermined frequencies selected so that said color complex modulated signal combines simultaneous slow and fast modulations.

9. The light modulation device according to claim 7, wherein the plurality of LFOs of said complex color modulation generator comprises a main LFO and at least one control LFO operatively connected to the main LFO for controlling at least one of waveform parameters of the oscillating signal therefrom.

10. The light modulation device according to claim 7, wherein the plurality of LFOs of said complex color modulation generator comprises:
a first modulation set including a main LFO and at least one control LFO operatively connected to the main LFO for controlling at least one of waveform parameters of the oscillating signal therefrom; and
a second modulation set including an additional LFO and at least one control LFO operatively connected to the additional LFO for controlling at least one of waveform parameters of the additional oscillating signal therefrom.

11. The light modulation device according to claim 7, wherein said intensity parameter is controlled by a base signal.

12. The light modulation device according to claim 7, wherein said intensity parameter is controlled by a simple modulated signal, the light modulation device comprising a simple modulation generator for generating the simple modulated signal, the simple modulation generator being in communication with the light modulator for providing the simple modulated signal thereto, said simple modulation generator having:
a main Low Frequency Oscillator (LFO) generating an oscillating signal; and
an intensity mixer multiplying said oscillating signal of the main LFO with a base signal, thereby providing said simple modulated signal.

13. The light modulation device according to claim 7, wherein said intensity parameter is controlled by an intensity complex modulated signal generated by a complex intensity modulation generator.

14. The light modulation device according to claim 13, wherein, for each of the complex intensity and color modulation generators, the plurality of LFOs comprises:
a first modulation set including a main LFO and at least one control LFO operatively connected to the main LFO for controlling at least one of waveform parameters of the oscillating signal therefrom; and
a second modulation set including an additional LFO and at least one control LFO operatively connected to the additional LFO for controlling at least one of waveform parameters of the additional oscillating signal therefrom;

for each of the complex intensity and color modulation generators, the oscillating signals of the main LFO and additional LFO having distinct predetermined frequencies selected so that the corresponding complex modulated signal combines simultaneous slow and fast modulations.

15. A light modulation device for generating modulated color component output signals adapted for use by a light projecting system for modulating light projected thereby, the light modulation device comprising:
an electronic circuit, comprising:
a light modulator generating said color component output signals according to an intensity parameter for controlling a brightness of said light and a color parameter for controlling a hue of said light, said intensity parameter being controlled by an intensity complex modulated signal; and
a complex intensity modulation generator generating said intensity complex modulated signal, the complex intensity modulation generator being in communication with the light modulator for providing the intensity complex modulated signal thereto, said complex intensity modulation generator having a plurality of Low Frequency Oscillators (LFO) each generating an oscillating signal, the intensity complex modulated signal resulting from a combination of the oscillating signals of each of said LFOs, wherein said complex intensity modulation generator comprising an intensity mixer multiplying the oscillating signal of at least one of said LFOs with a base intensity signal, said intensity mixer comprising a multiplicator such that:

$$I_{combined}(t)=I_b(t)*(1-I_{lfo}(t)/I_{range});$$

wherein t represents time, $I_{combined}$ is the combined intensity signal, $I_b(t)$ is the base intensity signal, $I_{lfo}(t)$ is the oscillating signal of the corresponding LFO and $I_{range}$ is a maximum authorized value for $I_b(t)$ and $I_{lfo}(t)$.

16. The light modulation device according to claim 15, wherein said color parameter is controlled by a color complex modulated signal, the electronic circuit further comprising a complex color modulation generator generating said color complex modulated signal, the complex color modulation generator being in communication with the light modulator for providing the color complex modulated signal thereto, wherein said complex color modulation generator comprising a color mixer performing a summation of the oscillating signal of at least one of said LFOs with a base color signal, thereby providing a combined color signal, said color mixer comprising a modulo summation element such that:

$$C_{combined}(t)=(C_b(t)+C_{lfo}(t)) \text{modulo } C_{range};$$

wherein t represents time, $C_{combined}(t)$ is the combined color signal, $C_b(t)$ is the base color signal, $C_{lfo}(t)$ is the oscillating signal of the corresponding LFO and $C_{range}$ is a maximum authorized value for $C_b(t)$ and $C_{lfo}(t)$.

* * * * *